US011817181B2

United States Patent
Wang et al.

(10) Patent No.: US 11,817,181 B2
(45) Date of Patent: Nov. 14, 2023

(54) METHOD FOR EVALUATING METABOLIZABLE ENERGY IN GOOSE DIET BY USING A SIMULATIVE DIGESTION GROSS ENERGY TECHNIQUE

(71) Applicant: South China Agricultural University, Guangzhou (CN)

(72) Inventors: Wence Wang, Guangzhou (CN); Lin Yang, Guangzhou (CN); Jing Yang, Guangzhou (CN); Yongwen Zhu, Guangzhou (CN); Hui Ye, Guangzhou (CN); Yu Li, Guangzhou (CN); Heng Wang, Guangzhou (CN); Daiyang Xia, Guangzhou (CN); Jianying Chen, Guangzhou (CN); Weiqing Ma, Guangzhou (CN); Yang Fu, Guangzhou (CN); Shanshan Zhu, Guangzhou (CN)

(73) Assignee: South China Agricultural University, Guangzhou (CN)

(*) Notice: Subject to any disclaimer, the term of this patent is extended or adjusted under 35 U.S.C. 154(b) by 241 days.

(21) Appl. No.: 17/303,513

(22) Filed: Jun. 1, 2021

(65) Prior Publication Data

US 2022/0020451 A1 Jan. 20, 2022

(30) Foreign Application Priority Data

Jul. 20, 2020 (CN) .......................... 202010697391.2

(51) Int. Cl.
G16B 40/00 (2019.01)
G16B 5/00 (2019.01)
(Continued)

(52) U.S. Cl.
CPC .............. *G16B 40/00* (2019.02); *C12Q 1/37* (2013.01); *C12Q 1/40* (2013.01); *G16B 5/00* (2019.02);
(Continued)

(58) Field of Classification Search
None
See application file for complete search history.

(56) References Cited

FOREIGN PATENT DOCUMENTS

| CN | 102590017 A | * | 7/2012 |
| CN | 103882094 A | * | 6/2014 |
| CN | 104313120 A | * | 1/2015 |

* cited by examiner

*Primary Examiner* — Robert J Yamasaki
*Assistant Examiner* — Charles Zoltan Constantine
(74) *Attorney, Agent, or Firm* — DLA PIPER LLP (US)

(57) ABSTRACT

Embodiments of the present disclosure belongs to the technical field of animal feed and provides a method for rapidly evaluating metabolizable energy of goose diet by using a technique of simulative digestion gross energy. By using the technical means combining the biological method and the simulative digestion gross energy technique, metabolizable energy of goose feed can be evaluated quickly. Based on the "stomach-small intestine" two-step enzymatic methods, it is the first time to establish a regression equation between the metabolizable energy change and fiber level in the cecum to rectify the value of simulative digestion gross energy in the cecal microbial digestion phase, making the simulative digestion gross energy technique more reasonable in the assessment of metabolizable energy in geese. Results show that the use of simulative digestion gross energy technique to assess the metabolizable energy of goose feed value is highly feasible.

16 Claims, 3 Drawing Sheets

(51) Int. Cl.
*C12Q 1/37* (2006.01)
*C12Q 1/40* (2006.01)
(52) U.S. Cl.
CPC .................. *G01N 2333/928* (2013.01); *G01N 2333/96416* (2013.01); *G01N 2333/976* (2013.01)

METHOD FOR EVALUATING METABOLIZABLE ENERGY IN GOOSE DIET BY USING A SIMULATIVE DIGESTION GROSS ENERGY TECHNIQUE

CROSS-REFERENCE TO RELATED APPLICATIONS

This application claims priority to Chinese Application Serial No. 202010697391.2, filed Jul. 20, 2020, which is herein incorporated by reference in its entirety.

TECHNICAL FIELD

The present disclosure relates to the technical field of animal feed, and in particular to a method for evaluating the metabolizable energy in goose diet by using a simulative digestion gross energy technique.

BACKGROUND

The nutritional value of nutrients is a key indicator to measure the quality of feed ingredients, and energy and protein, as the key research subjects of animal nutriology, are irreplaceable in the assessment of nutritional value. Due to the differences in physiological structure and nutritional requirements of animals of different species or different growth stages of the same species, the corresponding methods of nutritional value evaluation are quite different, making the nutritional value of the same sample in different animals widely different. For domestic animals, there are three types of energy systems that are used to evaluate diet: metabolizable energy, digestive energy, and net energy. The reason is that the nutritional requirements and digestive capacity are different in different periods. For example, sows can obtain a higher level of fiber and fat digestibility than the growing pigs. Therefore, factors such as maintenance heat production, active heat production and body temperature maintenance of animals need to be further taken into account in the evaluation of nutritional value. Compared with pigs, the nutritional value assessment system for poultry is simple, which is mainly based on the metabolizable energy system. Some scholars have tried to use artificial ostomy so that feces and urine of poultry can be collected separately like livestock, but the side effects resulting from the surgical operation prevent the animals from returning to their normal physiological state prior to the operation. Accurately assessing the nutritional value of diet can not only improve the production performance and reproductive capacity of animals but also greatly reduces the waste of feed resources. While reducing the environmental pollution caused by breeding from the source, it can also bring considerable benefits to breeding enterprises and farmers.

China is a big poultry farming country and tops the world in the annual number of live poultry produced for slaughter. However, the per capita consumption is much lower than that in developed countries. This means that there is still a huge room and potential for the development of domestic poultry breeding and poultry meat consumption. So far, China's databases for the nutritional value of feed were those created in the 1990s. In the latter times, the databases were revised by referring to the parameters in the Feedstuffs database, the French feed database, Degussa's amino acid database, which has been unable to meet our needs in the development of the animal nutrition field to some extent, and data on geese is even scarce. Goose is an omnivorous animal that can tolerate rough feeding, have strong disease resistance, and has a wide range of feeding. The breeding of geese has been carried out in a free-range breeding mode for a long time in the past. This is why the researches on the nutritional needs of geese are far behind that of pigs and chickens. With the development of society and the rise of people's living standards, people are more inclined to choose nutritious and healthy foods on the basis of solving the problem of food and clothing. Goose meat is very popular as an ideal high-protein, low-cholesterol and low-fat food. Under the huge market demand, the supply is difficult to meet the demand under the conditions of traditional breeding mode, which also means that its breeding mode must be changed from the traditional free-range breeding mode to an intensive breeding mode. However, lack of goose feeding standards and nutritional value of feed undoubtedly hinders the successful transformation of breeding mode. Therefore, the establishment of a quick and simple determination method under the premise of accurate data cannot only fill the gap of the nutritional value of goose feed but also has guiding significance for actual production.

Simulative digestion gross energy method is a method that is based on the in vivo digestive enzyme characteristics and simulates, to the maximum extent, the digestion of enzymes of diet in digestive tract on the basis of in vitro enzymatic methods. Therefore, the key technology of simulative digestion gross energy technique is to keep the enzymatic properties of in vitro digestion fluid consistent with endogenous digestion fluid. However, due to the differences in the physiological structure between mammals and poultry, the simulative digestion gross energy technique is different in evaluating animal feed metabolism. At the same time, the difference in digestive enzymes in the digestive system between different poultry leads to a substantive difference in feed metabolism process of geese feed between geese and other poultry animals such as chickens and ducks.

SUMMARY OF THE INVENTION

In view of this, the objective of the present disclosure is to provide a method for evaluating the metabolizable energy of goose diet by using a simulative digestion gross energy technique. The metabolizable energy of goose diet ingredients are measured by an in vitro digestion method in which the goose metabolizable energy is rapidly and accurately evaluated, thereby providing scientific guidance for the establishment of the formula of goose feed.

The present disclosure provides a method for rapidly evaluating metabolizable energy of goose diet by using a simulative digestion gross energy technique, and the method comprises the following steps:

(1) measuring and calculating a value of simulative digestion gross energy of the diet by using a simulative digestion gross energy technique;

the parameters used for measuring the diet by using the simulative digestion gross energy technique are as follows:

the digestive enzyme in the simulated gastric fluid is pepsin, and the concentration of the pepsin 1475 U/ml;

the digestive enzyme in the simulated intestinal fluid is selected from trypsin, chymotrypsin, and amylase; and every 2000 ml of the simulated intestinal fluid contains 0.1900 g of trypsin, 0.0526 g of chymotrypsin and 4.45 ml of amylase solution;

the digestion temperature both in gastric phase and in the intestinal phase is 40.5° C.-41.5° C.;

the digestion time in the gastric phase is 4-5 hours, and digestion time in the intestinal phase is 12-16 hours;

the value of simulative digestion gross energy is calculated by the following formula D;

$$\text{value of simulative digestion of gross energy} = \frac{\text{gross energy of diet} - \text{gross energy of residue}}{\text{mass of diet}} \quad \text{formula D}$$

wherein the unit of the value of simulative digestion gross energy is MJ/kg;

(2) putting the level (s) of crude fiber in the diet to be measured into formula E for rectifying the value of simulative digestion gross energy to obtain a rectified value of simulative digestion gross energy of the crude fiber in the diet;

rectified value of simulative digestion of gross energy=−0.020*CF$^2$+0.333*CF−0.476+SDGE    formula E:

wherein CF represents crude fiber, the unit of the rectified value of simulative digestion gross energy is MJ/kg, and SDGE represents the value of simulative digestion gross energy.

In some embodiments, the rectified value of simulative digestion gross energy is the sum of the value of simulative digestion gross energy and the value of simulative digestion gross energy of the crude fiber in the diet obtained by a curve model for rectifying the value of simulative digestion gross energy;

the curve model for rectifying the value of simulative digestion gross energy is a quadratic curve regression equation of the crude fiber in cecum against apparent metabolizable energy, constructed with the crude fiber being as an independent variable, and the equation is shown as formula C:

AMEI−AMEC=−0.020*CF 2+0.333*CF−0.476    formula C:

wherein AMEI represents the apparent metabolizable energy in intact geese, AMEC represents the apparent metabolizable energy in cecectomized geese, and CF represents the crude fiber.

In some embodiments, the mass of crude fiber accounts for 4-11% of the total mass of the diet, and the gross energy in the diet containing crude fiber is 18-22 MJ/kg.

In some embodiments, in step 1) the use of goose simulative digestion gross energy technique to measure the diet of one or more levels comprises simulated digestion in gastric phase and simulated digestion in intestinal phase;

when in the simulated digestion in the gastric phase, the flow rate of gastric phase buffer solution is 120 ml/min, and the gastric phase buffer solution contains 2.17 g of sodium chloride and 1.57 g of potassium chloride in every 2000 ml of the gastric phase buffer solution, and the gastric phase buffer solution has a pH value of 2.0 at a temperature of 40.5° C.-41.5° C.;

when in the simulated digestion in the intestinal phase, the flow rate of intestinal phase buffer solution is 120 ml/min, and the intestinal phase buffer solution contains 2.79 g of sodium chloride, 5.33 g of potassium chloride, 41.688 g of anhydrous sodium dihydrogen phosphate, 7.47 g of anhydrous disodium hydrogen phosphate and 1.6 million units of penicillin in every 2000 ml of intestinal phase buffer solution, and the intestinal phase buffer solution has a pH value of 6.38 at a temperature of 40.5° C.-41.5° C.

In some embodiments, in step 1), the method comprises a step of performing a correlation analysis between the value of simulative digestion gross energy and the value of apparent metabolizable energy measured by using an emptying forced feeding technique to obtain a correlation between the value of the apparent metabolizable energy and the value of simulative digestion gross energy, and the measuring accuracy of goose simulative digestion gross energy technique is higher than that of the emptying forced feeding technique, and the value of simulative digestion gross energy is used to construct a calculation formula for the rectified value of simulative digestion gross energy.

In some embodiments, the correlation coefficient between the value of apparent metabolizable energy and the value of simulative digestion gross energy is equal to or greater than 0.9.

In some embodiments, the coefficient of variation of the value of apparent metabolizable energy is 3.84-8.75%, and the coefficient of variation of the value of simulative digestion gross energy is 0.47-1.14%.

In some embodiments, the method of the present disclosure is applicable to a medium-sized goose.

In some embodiments, the ingredient of the crude fiber is at least one selected from corn, wheat, rice, wheat bran, and rice husk.

The present disclosure provides a method for evaluating the metabolizable energy of goose diet using simulative digestion gross energy technique. First, the complete diet is used as a research object, and the emptying forced feeding technique is used to evaluate the true metabolizable energy and the apparent metabolizable energy in cecectomized geese and in intact geese so as to evaluate the contribution of the cecum to the metabolizable energy. The results show that the nutrients in the diet can be utilized by the cecum. Since the simulative digestion of the gross energy technique is used to determine the simulative metabolizable energy subsequently, the absorption effect of cecum on feed needs to be considered. At the same time, because there is a substantial estimated deviation between SDGE and TME, the apparent metabolizable energy is used as the biological metabolizable energy of the goose for subsequent analysis. Then the crude fiber (CF) is used as an independent variable to construct a regression equation of crude fiber against the apparent metabolizable energy in the cecum. In the regression curves for CF against the apparent metabolizable energy in intact geese, against the apparent metabolizable energy in cecectomized geese, and the apparent metabolizable energy in the cecum, the quadratic curve has a bigger $R^2$ value than that of the linear equation, and the P value is less than 0.05, indicating that the quadratic curve is statistically significant. Meanwhile, to verify the simulative digestion gross energy technique and the emptying forced feeding technique in the present disclosure, the metabolizable energy of diet of the crude fiber of different levels is measured, and the correlation between the value of simulative digestion gross energy and the value of apparent metabolizable energy is analyzed. The results show that there is a strong correlation between the value of apparent metabolizable energy and the value of simulative digestion gross energy, and the measuring accuracy for the simulative digestion gross energy technique is higher than that for the emptying forced feeding technique. Therefore, the simulative method of the present disclosure may be used to measure the value of simulative digestion gross energy of the goose and to estimate the quantitative level of the apparent metabolizable energy in the biological method. Considering that the digestion of crude fiber in the diet by the cecum also produces a portion of apparent metabolizable energy, the rectified value of simulative digestion gross energy obtained by the curve model (apparent metabolizable energy in the cecum) for rectifying the value of simulative digestion gross energy technique obtained above and by the value of simulative digestion gross energy is used to evaluate the biological metabolizable energy of the diet. The method provided by the present disclosure can effectively and accurately evaluate the metabolizable energy of the diet in the goose body, thereby understanding the metabolism of different diets in the geese and providing scientific guidance for subsequent designation of compound goose feed formula.

To verify the feasibility of the method provided in the present disclosure for evaluating of metabolizable energy of goose diet, in the feed additivity test, the difference between the measured value and the calculated value of the apparent metabolizable energy of 13 formula diets measured by the simulative digestion gross energy technique falls within the range of 0.37-1.63 MJ/kg, and the percentage of the measured value over the calculated value is 102.87%-113.44%. There is a small difference between the measured value and the calculated value of SDGE, with the difference being within the range of −0.05-0.52 MJ/kg, and the percentage of the measured value over the calculated value being 99.12-104.18%, indicating that the additivity of the simulative digestion gross energy technique is better than that of the emptying forced feeding technique. It can be seen that the method provided in the present disclosure can also be used for evaluating the formula diet.

DETAILED DESCRIPTION OF THE EMBODIMENTS

Figure 1:
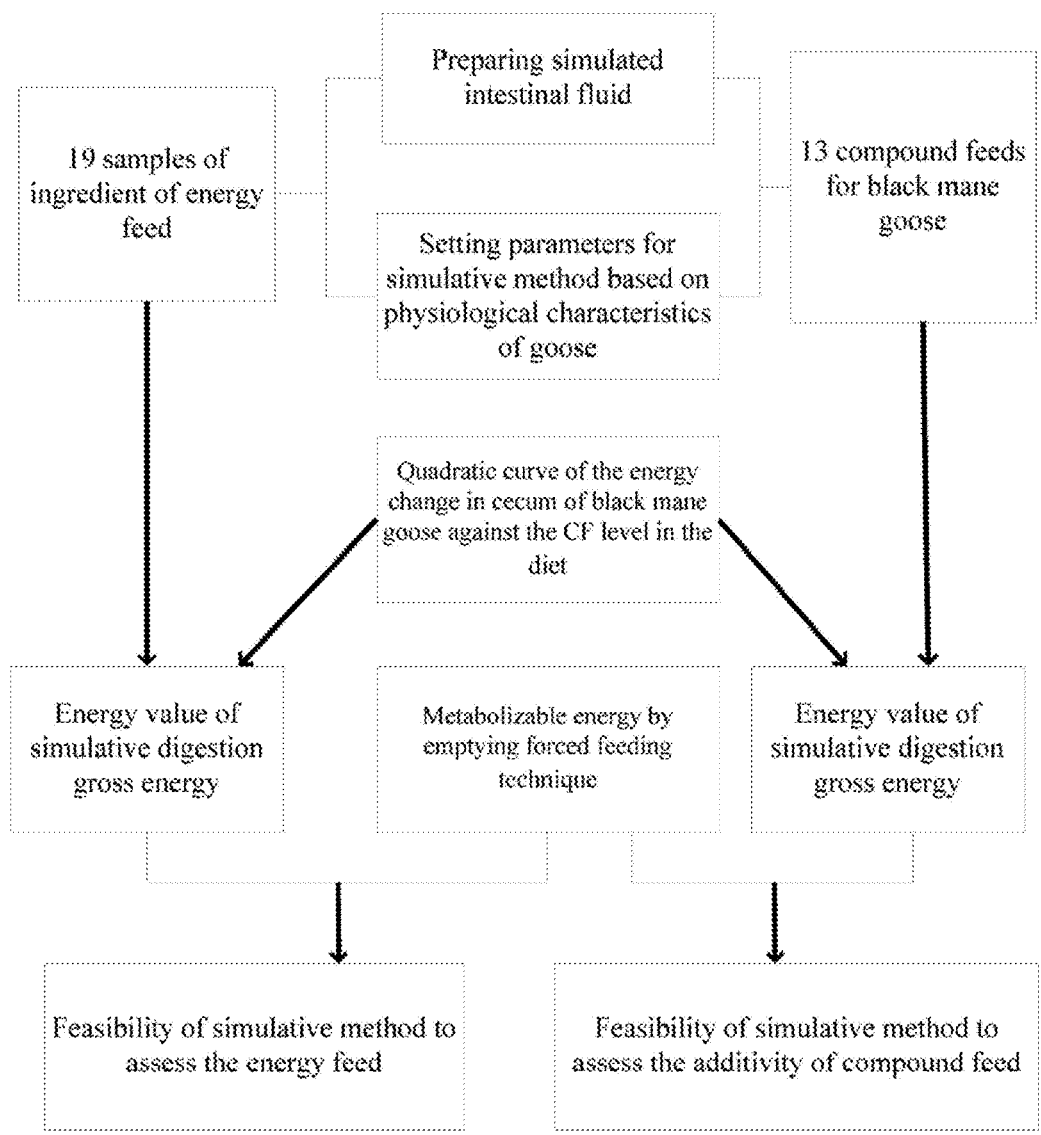
FIG. 1 is an experimental flow chart of the scheme of the present disclosure.
Figure 2:
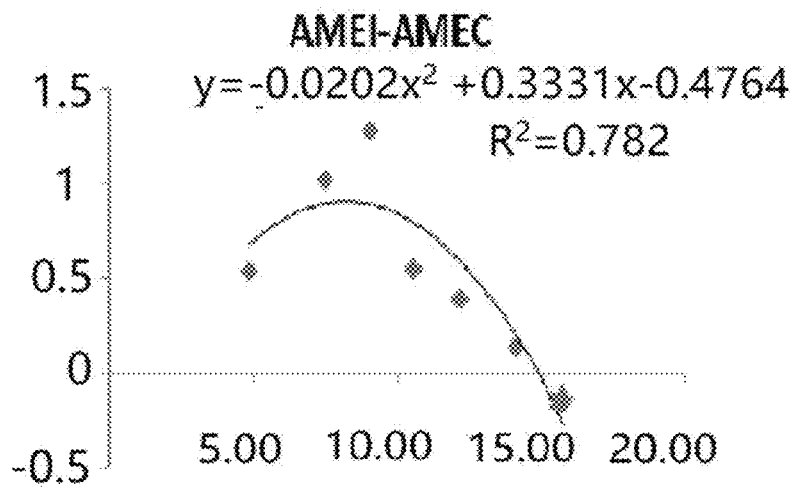
FIG. 2 shows a quadratic curve against the change of cecum energy value and the CF level.

The present disclosure provides a method for evaluating metabolizable energy of a goose diet by using simulative digestion gross energy technique, comprising the following steps:

1) measuring and calculating a value of simulative digestion gross energy for the diet of one or more fiber levels by using simulative digestion gross energy technique;

the value of simulative digestion gross energy is calculated by the following formula D;

$$\text{value of simulative digestion of gross energy} = \frac{\text{gross energy of diet} - \text{gross energy of residue}}{\text{mass of diet}} \quad \text{formula D}$$

wherein the unit of the value of simulative digestion gross energy is MJ/kg;

the parameters used for measuring the diet of one or more fiber levels by using the simulative digestion gross energy technique are as follows:

the digestive enzyme in the simulated gastric fluid is pepsin, and the concentration of the pepsin 1475 U/ml;

the digestive enzyme in the simulated intestinal fluid is selected from trypsin, chymotrypsin, and amylase; and every 2000 ml of the simulated intestinal fluid contains 0.1900 g of trypsin, 0.0526 g of chymotrypsin and 4.45 ml of amylase solution;

the digestion temperature both in the gastric phase and in intestinal phase is 40.5° C.-41.5° C.;

digestion time in the gastric phase is 4-5 hours, and digestion time in the intestinal phase is 12-16 hours;

(2) putting the level(s) of crude fiber in the diet to be measured into formula E for rectifying the value of simulative digestion gross energy to obtain a rectified value of simulative digestion gross energy of the crude fiber in the diet;

$$\text{rectified value of simulative digestion of gross energy} = -0.020*CF^2 + 0.333*CF - 0.476 + SDGE \quad \text{formula E;}$$

In the present disclosure, in order to investigate the effect of different levels of fiber in the diet and cecal resection on the metabolizable energy, firstly it is preferred to use an emptying force-feeding technique to feed a diet of at least one fiber level, and the true metabolizable energy and the apparent metabolizable energy in the cecectomized geese and in the intact geese are measured and calculated, and a regression analysis was performed on the levels of crude fiber versus the values of the two types of metabolizable energy consumed in the cecem, finding that the apparent metabolizable energy is negatively correlated with the fiber level of the diet.

In the present disclosure, the emptying forced feeding technique preferably includes a pre-feeding period of three days, fasting for 24 hours before the forced feeding, and free drinking during the entire experiment. 60 g of air-dried test feed is accurately fed, and fecal samples are collected within 48 hours. On the 11$^{th}$ day after the end of the experiment, endogenous feces are collected by using a starvation method.

In the present disclosure, the mass percentage of the crude fiber in the diets of at least one crude fiber level is preferably 4-11%; and the gross energy in the diets of at least one crude fiber level is preferably 18-22 MJ/kg. In order to fully simulate the content of crude fiber in the diet, the present disclosure uses complete feed for evaluation when feeding the cecectomized geese and the intact geese.

In the present disclosure, the apparent metabolizable energy is preferably calculated according to the following formula A; the true metabolizable energy is calculated according to the following formula B;

$$\text{apparent metabolizable energy} = \frac{\text{gross energy of diet} - \text{fecal energy}}{\text{mass of diet}} \quad \text{formula A}$$

Wherein the unit of apparent metabolizable energy is MJ/kg;

$$\text{true metabolizable energy} = \frac{\text{gross energy of diet} - \text{fecal energy} + \text{endogenous fecal energy}}{\text{mass of diet}} \quad \text{formula B}$$

where in the unit of true metabolizable energy is MJ/kg.

There are no special restrictions on the test methods of the diet gross energy, forced feeding fecal energy and endogenous fecal energy, and detection methods well known in the art may be used.

In the present disclosure, after the correlation analysis, the results showed that the correlation coefficient between the crude fiber and the apparent metabolizable energy in cecectomized geese was −0.81, the correlation coefficient between the crude fiber and the apparent metabolizable energy in intact geese was −0.77, indicating that there was a strongly negative correlation between the apparent metabolizable energy and the fiber level in the diet.

At the same time, the results showed that the apparent metabolizable energy and true metabolizable energy in the intact geese were higher than that in the cecectomized geese. Therefore, the value of apparent metabolizable energy measured by choosing the intact geese as the test animal is closer to the actual production level.

In the present disclosure, crude fiber is preferably used as an independent variable to construct a quadratic regression equation of crude fiber against apparent metabolizable energy in the cecum to obtain a curve model for rectifying the energy value of simulative digestion gross energy technique, as shown in formula C;

$$\text{AMEI-AMEC} = -0.020 * CF\ 2 + 0.333 * CF - 0.476 \quad \text{formula C:}$$

wherein AMEI represents the apparent metabolizable energy in intact geese, AMEC represents the apparent metabolizable energy in cecectomized geese, and CF represents the crude fiber.

In the present disclosure, the curve model for rectifying the energy value of simulative digestion gross energy technique is the difference between apparent metabolizable energy in the intact goose and cecectomized geese, that is, the value of apparent metabolizable energy in the cecum. The apparent metabolizable energy increases with the increase of fiber level, with the fiber levels increasing firstly and decreasing afterward. The simple correlation between the levels of other fibers (ADF, NDF, and ADL) and the apparent metabolizable energy is higher than that of CF. By using fiber as an independent variable to establish a linear regression equation and a quadratic regression equation for the apparent metabolizable energy. In the regression curves for CF against the metabolizable energy in intact geese, against the metabolizable energy in cecectomized geese, and against the difference between them, the quadratic curve has the biggest $R^2$ value than that of the linear equation, and the quadratic curve of CF against AMEI−AMEC has higher $R^2$ than ADF, NDF, ADL, and the P value is less than 0.05, indicating that the quadratic curve is statistically significant. Therefore, the curve model is subsequently used to rectify the value of simulative digestion gross energy.

In the present disclosure, in order to investigate the feasibility of the simulative digestion gross energy technique in predicting the metabolizable energy of the feed, an emptying forced feeding technique is used to measure and calculate to obtain the value of apparent metabolizable energy in goose for the diet of at least one fiber level, and simulative digestion gross energy technique is used to measure and calculate to obtain the value of simulative digestion gross energy of the diet of at least one fiber level. Through the correlation analysis, a correlation between the value of apparent metabolizable energy and the value of simulative digestion gross energy is obtained. The measuring accuracy of simulative digestion gross energy technique is higher than that of emptying forced feeding technique. The value of simulative digestion gross energy is calculated according to the following formula D;

$$SDGE = \frac{\text{gross energy of diet} - \text{gross energy of residue}}{\text{mass of diet}} \quad \text{formula D}$$

wherein the value of simulative digestion gross energy is abbreviated as SDGE and expressed in MJ/kg;

The parameters used for measuring the diet of one or more fiber levels by using the simulative digestion gross energy technique are as follows:

the digestive enzyme in the simulated gastric fluid is pepsin, and the concentration of the pepsin is 1475 U/ml;

the digestive enzyme in the simulated intestinal fluid is selected from trypsin, chymotrypsin, and amylase; and every 2000 ml of the simulated intestinal fluid contains 0.1900 g of trypsin, 0.0526 g of chymotrypsin and 4.45 ml of amylase solution;

the digestion temperature both in the gastric phase and in intestinal phase is in a range of 40.5° C.-41.5° C., preferably 40.5° C.;

the digestion time in the gastric phase is 4-5 hours, preferably 4 hours, and digestion time in the intestinal phase is in a range of 12-16 hours, preferably 14 hours.

In the present disclosure, when the simulative digestion gross energy technique is used to measure the diet of at least one fiber level, it is preferred to comprise simulated digestion in the gastric phase and simulated digestion in the intestinal phase;

when in the simulated digestion in the gastric phase, the flow rate of gastric phase buffer solution is 120 ml/min, and the gastric phase buffer solution contains 2.17 g of sodium chloride and 1.57 g of potassium chloride in every 2000 ml of the gastric phase buffer solution, and the gastric phase buffer solution has a pH value of 2.0 at a temperature of 40.5° C.-41.5° C.;

when in the simulated digestion in the intestinal phase, the flow rate of intestinal phase buffer solution is 120 ml/min, and the intestinal phase buffer solution contains 2.79 g of sodium chloride, 5.33 g of potassium chloride, 41.688 g of anhydrous sodium dihydrogen phosphate, 7.47 g of anhydrous disodium hydrogen phosphate and 1.6 million units of penicillin in every 2000 ml of intestinal phase buffer solution, and the intestinal phase buffer solution has a pH value of 6.38 at the temperature of 40.5° C.-41.5° C.

In the present disclosure, the correlation coefficient between the value of apparent metabolizable energy and the value of simulative digestion gross energy is preferably up to 0.9 or more, the simulative digestion gross energy technique is extremely highly correlated with the value of emptying forced feeding technique. The diet is preferably wheat or corn. The coefficient of variation of the value of apparent metabolizable energy determined by a biological method is preferably 2.5-5.0%, coefficient of variation of the value of simulative digestion gross energy is preferably 0.47%-1.14%. Specifically, by comparing the measuring accuracy of 19 tested feed samples, it can be seen that the coefficient of variation of AME measured by biological methods are all below 7.5%, but all are higher than 1.0%. Among them, the coefficients of variation of AME are mainly concentrated between 2.5-5.0%, AME accounts for 84.21% in this range. The coefficient of variation of SDGE determined by the simulative digestion gross energy technique were all below 2.5%, and among them, the SDGE coefficients of variation of 10 samples were all below 1.0%, accounting for 52.63% of the total number of samples. It indicates that the measuring accuracy of the simulative digestion gross energy technique is higher than that of the emptying forced feeding technique, and the coefficients of variation of the value of simulative digestion gross energy (SDGE) are smaller than the apparent metabolizable energy corresponding to the emptying forced feeding technique.

In the present disclosure, after obtaining the curve model for rectifying the value of simulative digestion gross energy technique and the value of simulative digestion gross energy of the crude fiber in the diet, the crude fiber levels of the diet to be measured were put into the formula E for rectifying the values of simulative digestion gross energy to give a rectified value of simulative digestion gross energy for the crude fiber in the diet, the formula E is obtained by a curve model for rectifying the value of simulative digestion gross energy technique and the value of simulative digestion gross energy of crude fiber in diet:

rectified value of simulative digestion of gross energy=$-0.020*CF^2+0.333*CF-0.476+SDGE$    formula E wherein CF is crude fiber, and the unit of the rectified value of simulative digestion gross energy is MJ/kg.

In the present disclosure, compared with the value of simulative digestion gross energy and the rectified value of simulative digestion gross energy, the estimated deviation of the rectified value of simulative digestion gross energy (SDGE 2) of corn, wheat and rice from the apparent metabolizable energy reaches a quantitative level as to estimation of the apparent metabolizable energy by a biological method, thus the rectified value of simulative digestion gross energy may be used to evaluate the metabolizable energy of goose feed in vitro.

The rectified value of simulative digestion gross energy is shown in formula F;

rectified value of simulative digestion of gross energy=SDGE+0.74    formula F:

wherein SDGE represents the value of simulative digestion gross energy, 0.74 is the mean of change in energy value in the cecum obtained from the difference between apparent metabolizable energy in intact geese and in the intact geese at a suitable crude fiber level, and the unit of the rectified value of simulative digestion gross energy is MJ/kg.

There is no particular limitation to goose type in the present disclosure, and the method of the present disclosure applies to the evaluation of feed for all types of goose. The embodiments of the present disclosure are described by selecting the type of black mane goose as a representative.

The method for evaluating metabolizable energy of a goose diet by using simulative digestion gross energy technique provided in the present disclosure will be described in detail in combination with the embodiments. However, those embodiments shall not be construed as limitation to the protection scope of the present disclosure.

Abbreviations are listed below:

| Abbreviation | Full form |
| --- | --- |
| ADF | acid detergent fiber |
| ADL | acid detergent lignin |
| AME | apparent metabolizable energy |
| AMEC | apparent metabolizable energy in cecectomized geese |
| AMEI | apparent metabolizable energy in intact geese |
| CF | crude fiber |
| CV | coefficientofvariance |
| GE | gross energy |
| ME | metabolizable energy |
| NDF | neutral detergent fiber |
| SDGE | simulative digestion gross energy |
| TME | true metabolizable energy |

Example 1

1. Materials and Methods (1) Feed Ingredients

Corn and soybean meals were selected to determine the effect of temperature changes within the physiological range on nutrient digestibility of feed, and corn and peanut meal were selected to determine the effect of digestion time on nutrient digestibility of feed. Corn, soybean meal and peanut meal were crushed and passed through a 40-mesh sieve, and their chemical composition was determined after being homogenously mixed (see Table 1).

TABLE 1

Nutritional composition of feed ingredients (on air-dried matter basis, %)

| | nutrient content | | | | | | |
| --- | --- | --- | --- | --- | --- | --- | --- |
| Feed ingredient | Crude protein CP | gross energy GE | crude fiber CF | crude ash Ash | calcium Ca | phosphorus P | Dry matter DM |
| Corn | 7.69 | 15.97 | 2.91 | 1.62 | 0.02 | 0.27 | 88.72 |
| Soybean meal | 41.74 | 17.06 | 4.93 | 5.23 | 0.33 | 0.62 | 90.10 |
| Peanut meal | 46.35 | 17.50 | 8.49 | 5.49 | 2.93 | 0.70 | 89.79 |

(2) Measurement of Body Temperature in the Test Animal

Twenty healthy adult black mane geese were randomly selected and subjected to a rectal temperature measurement for 3 days. In order to reduce the measurement error caused by stress, measurement was conducted in three periods of morning (8:30-9:30) and noon (12:00)-13:00) and evening (17:30 to 18:30) on the first day and the third day, the temperature measurement data are shown in Table 2.

TABLE 2

| | Body temperature of adult male black mane geese (° C.) | | | | | |
|---|---|---|---|---|---|---|
| | day 1 | | | day 3 | | |
| time | mean | Standard deviation SD | Coefficient of Variation CV | mean | Standard deviation SD | Coefficient of Variation CV |
| morning | 41.07 | 0.34 | 0.83 | 41.05 | 0.41 | 1.00 |
| noon | 41.31 | 0.31 | 0.75 | 41.05 | 0.53 | 1.29 |
| evening | 41.13 | 0.49 | 1.19 | 41.08 | 0.29 | 0.71 |

(3) Preparation of Simulated Digestive Solution and Buffers for Simulative Digestion Gross Energy Technique By measuring the rectal temperature of black mane goose, an average temperature of 41° C. was obtained and the average temperature range was 40.5-41.5° C.

Preparation of simulated gastric fluid: A certain amount of pepsin (Sigma P7000) was weighed and dissolved with a pH 2.0 hydrochloric acid solution, and made up to 250 ml in a volumetric flask. The concentration of pepsin in the volumetric flask was 1475 U/ml.

Preparation of simulated intestinal fluid: simulated intestinal fluid was calculated via the in vivo activity of goose digestive enzyme, and 0.1900 g of trypsin (Amresco 0458), 0.0526 g of chymotrypsin (Amresco 0164) and 4.45 ml of amylase from (Sigma A3306) were mixed and made up to 2000 mL with water.

Preparation of simulated gastric phase buffer: 2.17 g of sodium chloride and 1.57 g of potassium chloride were weighed and dissolved in a 2000 ml beaker. Deionized water was added, the pH was adjusted to 2.0 at a certain temperature (three treatment temperatures: 40.5° C., 41.0° C. and 41.5° C.), and made up to 2000 ml after cooling and left for later use.

Preparation of simulated intestinal phase buffer: 2.79 g of sodium chloride, 5.33 g of potassium chloride, 41.688 g of anhydrous sodium dihydrogen phosphate anhydrous, 7.47 g of anhydrous disodium hydrogen phosphate and 1.6 million units of penicillin were weighed and dissolved in deionized water in a 2000 ml beaker with the aid of a magnetic stirrer (IKA), and the pH was adjusted to 6.38 at a certain temperature (three processing temperatures: 40.5° C., 41.0° C. and 41.5° C.). After cooling, the resulting solution was made up to 2000 ml for later use.

(4) Steps of Simulative Digestion

Preparation before the experiment: a dialysis bag (MEMBRA-CEL MD34-14 Da, Viskase, USA) was cut into small pieces of about 25 cm and the dialysis bag was boiled for 10 minutes in a 2 L solution of sodium bicarbonate and 1 mmol/L ethylenediaminetetraacetic acid disodium salt (pH=8.0), with a mass-volume ratio being 2%. After the dialysis bag was thoroughly cleaned with distilled water, the dialysis bag was put into a 1 mmol/L edetate disodium solution with pH=8.0 and continued to be boiled for additional 10 minutes. After the dialysis bag was cooled, the dialysis bag was stored at 4° C. together with the EDTA solution, ensuring that the dialysis bag was completely immersed in the EDTA solution before use. The dialysis bag was rinsed with deionized water 3 times before use.

Preparation and sample loading: the gastric phase buffer solution and the intestinal phase buffer solution were put into the constant temperature water tank of the monogastric animal simulative digestion system, and pipelines of the system were connected to the buffer bottles. Setup was made to allow the monogastric animal simulative digestive system to enter a 60-minute warm-up period. The treated dialysis bag was passed across the simulated digestive tube, with both ends flipped outward and both ends of the dialysis bag fixed with rubber bands. After rinsing the dialysis bag three times with deionized water, one end of the dialysis bag was plugged tightly with a turn-over silicone plug. The loading amount of samples in each digestive tube was 1 g for protein feed, 2 g for energy feed and 2 g for compound feed, respectively (accuracy of balance was 0.001 g).

Simulated gastric digestion: 20 ml of simulated gastric fluid was added to the dialysis bag by using a 5 ml pipette. The other end of the digestive tube was tightly plugged with a turn-over silicone plug with a digestive fluid addition tube containing digestive fluid. The digestive tube was placed into the constant temperature incubation shaker for the monogastric animal simulative digestion system to which, the buffer solution and enzyme solution pipelines were connected in such a manner that the 5 simulated digestive tubes were connected in series in the group. The parameters for the gastric phase simulated digestion were as follows: the buffer temperature was the same as the temperature for pH adjustment when preparing the buffer, the flow rate of the buffer was 120 ml/min, the digestion time was 4 hours, the amount of wash solution was 1500 ml/wash, and washing was conducted for 3 times with washing time of 40 min for each wash.

Simulated intestinal phase digestion: at the end of the simulated gastric digestion, 2.0 ml of simulated small intestinal fluid was accurately added into the small intestinal digestive fluid storage chamber. The parameters for simulated digestion in the small intestine phase were as follows: the buffer temperature was the same as the temperature for pH adjustment when preparing the buffer, the flow rate of the buffer was 120 ml/min, and the digestion time in the intestinal phase was to be determined. After the digestion was completed, washing solution was set to be 1500 ml of each time, and washing was conducted a total of 6 times, 40 minutes for each wash.

Treatment of digestion residue: after completion of the digestion, the undigested residue in the dialysis bag was transferred to a culture dish having known absolute dry weight without loss. The culture dish was dried at 65° C. and then transferred to 105° C. and dried to constant weight. The residue in the culture dish was scraped without loss and transferred to a sand core crucible having known absolute dry weight, and the residue was rinsed with absolute ethanol about 3 times (about 25 mL for each time) until the filtrate became colorless. At the same time, the culture dish with residue and the sand core crucible with defatted undigested residue were placed in a constant-temperature oven at 105° C. and dried to constant weight. The sample of defatted and undigested residue in the sand core crucible was transferred to a piece of nitrogen-free weighing paper on an oxygen bomb calorimeter and the energy value was measured. At the same time, the glass sand core crucible containing the residue of defatted residue was placed in a constant temperature oven at 105° C. and dried to constant weight.

(5) Steps to Assess the Effect of Temperature Changes on Simulative Digestion Gross Energy Technique and the Digestibility of Dry Matter In the study in which temperature change on the nutrient digestibility was determined at the physiological level, the digestion time of pepsin, trypsin+chymotrypsin, and amylase was 4 hours. Treatment 1 corresponded to the gastric phase buffer, and Treatment 2 and Treatment 3 corresponded to the intestinal phase buffer, respectively. The specific treatment method is shown in Table 3.

TABLE 3

Treatment conditions for determining the effect of different temperature on simulative digestion gross energy and dry matter utility rate

| | gastric phase | | | intestinal phase | | | |
|---|---|---|---|---|---|---|---|
| Treatment | time h | pepsin U/ml | pH | time h | trypsin g | chymotrypsin g | amylase ml | pH |
| Treatment 1 | 4 | 1475 | 2.0 | — | — | — | — | — |
| Treatment 2 | — | — | — | 4 | 0.1900 | 0.0526 | — | 6.38 |
| Treatment 3 | — | — | — | 4 | — | — | 4.45 | 6.38 |

(6) Statistical Analysis

A single-factor completely randomized test design was adopted in this test adopts and the GLM module of SAS software (SAS Institute, 2000) was used for analysis. When the difference was significant, Duncan multiple comparisons were used. The difference was shown to be significant when P<0.05.

2. Results and Analysis (1) Effect of In Vitro Enzymes on Simulative Digestion Gross Energy of Diet and Dry Matter Digestibility at Different Temperatures Table 4 shows the effect of temperature fluctuation on the change in simulative digestion gross energy. Pepsin in the gastric phase and amylase in the intestinal phase have no significant effect on the value of simulative digestion gross energy of the corm at different temperatures, while the value of simulative digestion gross energy for Trypsin+Chymotrypsin against the diet at 41.5° C. in the intestinal phase is significantly higher than at 40.5° C. At different temperatures, various digestive enzymes have no significant effect on the value of simulative digestion gross energy of the soybean meal.

It can be seen from Table 5 that pepsin in the gastric phase has no significant effect on dry matter digestibility of corn at different temperatures, while the digestibility for Trypsin+Chymotrypsin and amylase in the intestinal phase against the dry matter of the diet at 41.5° C. is significantly higher than that under the condition at 40.5° C. As far as soybean meal is concerned, the temperature has no significant effect on dry matter digestibility.

Within a digestion time of 4 hours, dry matter digestibility by protease for the corm as energy feed is 10% or less, the corresponding simulative digestion gross energy is 3 MJ/kg or less, while the digestibility of amylase on dry matter of corn is as high as 59%, the corresponding simulative digestion gross energy can reach 10 MJ/kg or more. In contrast, within the same digestion time, the dry matter digestibility of soybean meal as protein feed by protease is 42% for pepsin and 33% for trypsin+chymotrypsin, and the corresponding simulative digestion gross energy is 6.5 MJ/kg or more, while the dry matter digestibility of soybean meal by amylase is only about 23%, and the corresponding simulative digestion gross energy is less than 4 MJ/kg, which reflects the similar specificity of in vitro enzymes and digestive enzymes in vivo.

(2) Influence of Digestion Time in Intestinal Phase on Simulative Digestion Gross Energy and Dry Matter Digestibility of the Diet As shown in Table 6, after 10-22 hours of digestion in the intestinal phase, the value of simulative digestion gross energy of corn is 12.96-13.12 MJ/kg, the energy utilization rate is 72.44-73.67%, and the dry matter utility rate is 77.91-79.06%, different digestion time has no significant effect on simulative digestion gross energy and energy utility rate of corn, but has significant effect (P<0.05) on dry matter digestibility of the corn. The digestion time corresponding to maximum and minimum of the dry matter utility rate are 22 h and 14 h, respectively. After a digestion time of 10-22 hours, the value of simulative digestion gross energy of the soybean meal is 14.57-15.13 MJ/kg, the energy utilization rate is 74.63-77.65%, and the dry matter utility rate is 45.52-51.90% Different digestion time has a significant effect on the simulative digestion gross energy, the energy utilization rate and the dry matter digestibility of peanut meal (P<0.05). With the extension of digestion time, the indicators do not show a specific trend. The digestion time corresponding to the maximum and minimum simulative digestion gross energy is 16 h and 10 h, respectively, the digestion time corresponding to the maximum and minimum utility rate of simulative digestion gross energy is 16 h and 12 h, respectively, and the digestion time corresponding to the maximum and minimum dry matter digestibility is 14 h and 10 h, respectively.

TABLE 4

Effect of temperature change on the value of simulative digestion gross energy of the feed (on dry matter basis, MJ/kg)

| Treatment | Corn | | | Soybean meal | | |
| --- | --- | --- | --- | --- | --- | --- |
| | 40.5° C. | 41.0° C. | 41.5° C. | 40.5° C. | 41.0° C. | 41.5° C. |
| Treatment 1 | 2.52 ± 0.22 | 2.44 ± 0.15 | 2.39 ± 0.06 | 8.04 ± 0.07 | 8.00 ± 0.08 | 7.99 ± 0.04 |
| Treatment 2 | 2.04 ± 0.24 $^a$ | 2.45 ± 0.29 $^{ab}$ | 2.67 ± 0.23 $^b$ | 6.53 ± 0.02 | 6.61 ± 0.02 | 6.66 ± 0.08 |
| Treatment 3 | 10.29 ± 0.28 | 10.28 ± 0.25 | 10.48 ± 0.09 | 3.60 ± 0.20 | 3.60 ± 0.21 | 3.81 ± 0.17 |

Note:
Under the same conditions, the values, accompanying lowercase letters in the superscript or undenoted, in the same row indicate insignificant difference ($P > 0.05$).

TABLE 5

Effect of temperature change on dry matter digestibility of feed in the simulative digestion gross energy technique (on dry matter basis, %)

| Treatment | Corn | | | Soybean meal | | |
| --- | --- | --- | --- | --- | --- | --- |
| | 40.5° C. | 41.0° C. | 41.5° C. | 40.5° C. | 41.0° C. | 41.5° C. |
| Treatment 1 | 9.12 ± 0.38 | 9.19 ± 0.32 | 9.21 ± 0.12 | 42.69 ± 0.33 | 42.53 ± 0.48 | 42.45 ± 0.77 |
| Treatment 2 | 7.17 ± 0.44 $^b$ | 8.23 ± 0.45 $^a$ | 8.75 ± 0.36 $^a$ | 33.56 ± 0.96 | 34.52 ± 0.80 | 34.97 ± 0.71 |
| Treatment 3 | 59.22 ± 0.22 $^b$ | 60.15 ± 0.17 $^{ab}$ | 60.27 ± 0.62 $^a$ | 22.10 ± 0.30 | 22.85 ± 0.25 | 23.19 ± 0.51 |

Note:
Under the same conditions, the values, accompanying lowercase letters in the superscript or undenoted, in the same row indicate insignificant difference ($P > 0.05$).

TABLE 6

Effect of digestion time on simulative digestion of gross energy and on dry matter digestibility of the diet (on dry matter basis)

| Digestion time | Corn | | | Peanut meal | | |
| --- | --- | --- | --- | --- | --- | --- |
| | SDGE MJ/kg | SYGE % | SDDM % | SDGE MJ/kg | SYGE % | SDDM % |
| 10 h | 13.09 ± 0.24 | 73.67 ± 0.49 | 78.56 ± 0.62 $^{ab}$ | 14.57 ± 0.19 $^b$ | 75.11 ± 0.74 $^c$ | 45.52 ± 0.83 $^c$ |
| 12 h | 12.99 ± 0.12 | 72.56 ± 0.68 | 77.91 ± 0.46 $^b$ | 14.67 ± 0.20 $^b$ | 74.63 ± 0.47 $^c$ | 46.29 ± 0.31 $^c$ |
| 14 h | 13.03 ± 0.10 | 72.79 ± 0.56 | 78.47 ± 0.17 $^{ab}$ | 15.06 ± 0.26 $^a$ | 76.87 ± 0.6 $^{ab}$ | 51.90 ± 0.47 $^a$ |
| 16 h | 12.96 ± 0.27 | 72.44 ± 0.45 | 78.28 ± 0.31 $^b$ | 15.13 ± 0.09 $^a$ | 77.65 ± 0.50 $^a$ | 50.98 ± 0.92 $^a$ |
| 22 h | 13.12 ± 0.12 | 73.26 ± 0.69 | 79.06 ± 0.65 $^a$ | 14.79 ± 0.28 $^{ab}$ | 76.08 ± 0.56 $^{bc}$ | 48.63 ± 0.86 $^b$ |
| P value | 0.7116 | 0.0549 | 0.0203 | 0.0076 | 0.0033 | <0.0001 |

Note:
Under the same conditions, the values, accompanying lowercase letters in the superscript or undenoted, in the same column indicate insignificant difference ($P > 0.05$).

Example 2

1. Materials and Methods (1) Test Animals and Feeding Management

Twenty-one normal geese and Twenty-one cecectomized geese of 180-day-old and similar body weight (average weight of 4.1 kg), 21 geese for each group were selected and raised in a single cage in a metabolic cage. The geese were left to intake food and drink freely, with an illumination time of being 16 hours. Feeding management was carried out by referring to the routine feeding management procedures of South China Agricultural University (Animal Feed Science and Technology, 2017, 236: 115-121)

(2) Cecal Resection and Nursing

Eighty black male geese, 16 weeks old, having similar genetic background and body weight, were selected and raised in a single cage in a metabolic cage (45 cm×40 cm×85 cm). The geese were left to intake food and drink freely, with an illumination time of being 16 hours. After being raised in a metabolic cage for 7 days, cecectomy was performed on the geese. The procedure of cecal resection may be referred to Zhao Feng et al. (2006) and Wang et al. (2008). The processes for disinfection, suture and nursing were the same as that for fistula surgery, with the difference that the ileocecal valve was found after incision of the peritoneum during cecal resection. The cecum was ligated and taken out with #4 sutures at 1 cm away from the ileocecal valve, and the wound was coated with penicillin powder. The nursing process may be referred to conventional methods. At day 8 after the surgery, sutures at the goose abdominal were removed, and foot bands were attached and then the geese were fed together with the cecectomised geese till sexual maturity.

(3) Test Design and Diet

Test 1: a 2×3 (cecum×fiber) completely random design was used in this test. The test geese were fed with three species of diet having equal energy and equal nitrogen fiber containing 2.10%, 8.77% and 15.40% rice husk, corresponding to L, M and H groups. See Table 7 for diet compositions and nutritional levels. In the southern region of China, some farmers use rice as feed for the goose fattening period. Not only because the rice is more palatable than compound feed, but also the fiber in the rice husk meet and suits the nutritional needs of the goose fattening period, thus the rice husk was used as the main fiber source in this test.

Twenty-one adult cecectomized geese and intact geese were selected and divided into 6 groups (3 groups each for cecectomized geese and intact geese), each group had 7 replicates, each replicate included 1 goose, each group of of geese were fed with diets of different fiber level. The Sibbald emptying forced feeding technique was adopted, and the pre-feeding period was three days. The geese were fasted for 24 hours before force-feeding, and drinking water was freely fed throughout the test period. 60 g air-dried test material was precisely fed, and fecal samples within 48 h were collected. On the 11$^{th}$ day after the end of the test, a starvation method was used to collect endogenous feces.

TABLE 7

Diet composition and nutrient level (on air-dried matter basis, %)

| Diet | L | M | H |
|---|---|---|---|
| Composition | | | |
| Corn | 46.63 | 35.00 | 28.52 |
| Corn starch | 5.00 | 5.00 | 5.00 |
| Wheat | 15.22 | 15.14 | 15.00 |
| Wheat bran | 6.80 | 6.80 | 6.80 |
| Soybean meal | 3.12 | 4.86 | 5.7 |
| Rapeseed meal | 15.00 | 15.00 | 15.00 |
| Fat powder | — | 3.66 | 5.60 |
| Rice husk | 2.10 | 8.77 | 15.40 |
| Methionine | 0.16 | 0.17 | 0.18 |

TABLE 7-continued

Diet composition and nutrient level (on air-dried matter basis, %)

| Diet | L | M | H |
|---|---|---|---|
| Lysine Hydrochloride | 0.36 | 0.35 | 0.33 |
| Stone powder | 1.05 | 0.98 | 0.92 |
| Dicalcium Phosphate | 1.24 | 1.25 | 1.23 |
| Salt | 0.22 | 0.22 | 0.22 |
| Premix | 0.10 | 0.10 | 0.10 |
| Zeolite powder | 3.00 | 2.70 | — |
| Total | 100.00 | 100.00 | 100.00 |
| Nutrient content | | | |
| Crude Protein CP $^2$ | 15.26 | 14.94 | 14.97 |
| Crude fiber CF $^2$ | 4.45 | 7.69 | 11.02 |
| Neutral detergent fiber NDF $^2$ | 9.82 | 12.60 | 15.20 |
| Acid detergent fiber ADF $^2$ | 4.69 | 7.32 | 9.00 |
| Calcium Ca$^3$ | 0.82 | 0.82 | 0.78 |
| Available phosphorus | 0.65 | 0.65 | 0.62 |

Note:
[1] the premixed material provides the following ingredients for every kg of diet: VA 12000 IU; VD3 3000IU; VE 30 mg; VK3 6 mg; VB1 3 mg; VB2 9 mg of; VB6 6 mg; of VB12 0.03 mg; D-pantothenic acid 18 mg of; niacin 60 mg; folic acid 1.5 mg; biotin 0.15 mg; Fe 80 mg; Cu 8 mg; Mn 96 mg; Zn 80 mg; Co 0.32 mg; Se 0.32 mg; I 0.56 mg.
[2] Measured value: the measured value can be seen from the data denoted 2 in the upper right corner of Table 7.
[3] Calculated value

TABLE 8

Composition and nutritional level of diet of different fiber levels (on air-dried matter basis, %)

| Diet | 1 | 2 | 3 | 4 | 5 | 6 | 7 |
|---|---|---|---|---|---|---|---|
| Corn | 67.77 | 61.34 | 54.80 | 48.37 | 41.76 | 35.31 | 28.87 |
| Soybean meal | 20.90 | 21.90 | 23.00 | 24.05 | 25.15 | 26.20 | 27.20 |
| Rice husk | 2.20 | 5.50 | 8.73 | 12.00 | 15.25 | 18.50 | 21.75 |
| Wheat bran | 6.00 | 6.00 | 6.00 | 6.00 | 6.00 | 6.00 | 6.00 |
| Fat powder | 0.00 | 2.20 | 4.43 | 6.60 | 8.90 | 11.10 | 13.30 |
| Methionine | 0.17 | 0.18 | 0.18 | 0.19 | 0.20 | 0.20 | 0.21 |
| Lysine Hydrochloride | 0.10 | 0.09 | 0.07 | 0.05 | 0.03 | 0.02 | 0.00 |
| Stone powder | 1.07 | 1.00 | 1.00 | 0.95 | 0.90 | 0.85 | 0.80 |
| Dicalcium Phosphate | 1.42 | 1.42 | 1.42 | 1.42 | 1.45 | 1.45 | 1.50 |
| Salt | 0.27 | 0.27 | 0.27 | 0.27 | 0.27 | 0.27 | 0.27 |
| Premix material | 0.10 | 0.10 | 0.10 | 0.10 | 0.10 | 0.10 | 0.10 |
| total | 100.00 | 100.00 | 100.00 | 100.00 | 100.00 | 100.00 | 100.00 |
| Nutritional level | | | | | | | |
| Metabolizable energy ME (MJ/Kg)$^2$ | 11.67 | 11.66 | 11.66 | 11.64 | 11.66 | 11.65 | 11.64 |
| Crude protein CP (%)$^2$ | 15.02 | 15.01 | 15.01 | 15.01 | 15.02 | 15.02 | 15.00 |
| Calcium (%)$^2$ | 0.81 | 0.80 | 0.81 | 0.80 | 0.80 | 0.80 | 0.80 |
| Phosphorus P (%)$^2$ | 0.63 | 0.63 | 0.62 | 0.62 | 0.63 | 0.62 | 0.63 |
| Non-phytate phosphorus N-Phy-P (%)$^2$ | 0.40 | 0.40 | 0.39 | 0.39 | 0.39 | 0.39 | 0.40 |
| Lysine Lys (%)$^2$ | 0.83 | 0.83 | 0.83 | 0.83 | 0.83 | 0.83 | 0.83 |

TABLE 8-continued

Composition and nutritional level of diet of different fiber levels (on air-dried matter basis, %)

| Diet | 1 | 2 | 3 | 4 | 5 | 6 | 7 |
|---|---|---|---|---|---|---|---|
| Methionine Met (%)[2] | 0.40 | 0.41 | 0.40 | 0.41 | 0.41 | 0.41 | 0.42 |
| Methionine + cystine Met + Cys (%)[2] | 0.65 | 0.66 | 0.65 | 0.65 | 0.65 | 0.65 | 0.65 |

Note:
[1] the premixed material provides the following ingredients for every kgof diet: VA 12000 IU; VD3 3000IU; VE 30 mg; VK3 6 mg; VB1 3 mg; VB2 9 mg of; VB6 6 mg; of VB12 0.03 mg; D-pantothenic acid 18 mg of; niacin 60 mg; folic acid 1.5 mg; biotin 0.15 mg. Fe 80 mg; Cu 8 mg; Mn 96 mg; Zn 80 mg; Co 0.32 mg; Se 0.32 mg; I 0.56 mg.

2. Calculated Value

Test 2: This test was carried out to verify the metabolizable energy results of the cecectomized and intact geese in Test 1 to evaluate the contribution of the cecum to the metabolizable energy, and to perform a regression analysis on the level of crude fiber and the energy consumed in the cecum. 2×7 (cecum×fiber) completely randomized test design was used in the test, 7 addition levels of the rice husk were 2.20%, 5.50%, 8.73%, 12.00%, 15.25%, 18.50% and 21.75%, and the diets were numbered from No. 1 to No. 7. See Table 9 for diet composition, nutritional level and fiber level.

TABLE 9

Fiber level, dry matter content and gross energy of the seven diets (on air dry matter basis)

| GE (MJ/KG) | 18.06 | 18.67 | 19.16 | 19.64 | 20.15 | 20.81 | 21.47 |
|---|---|---|---|---|---|---|---|
| NDF (%) | 13.26 | 15.06 | 20.63 | 24.82 | 25.77 | 33.62 | 37 |
| ADF (%) | 5.72 | 7.32 | 10.94 | 14.73 | 16.19 | 20.99 | 24.53 |
| ADL (%) | 0.83 | 1.73 | 3.26 | 4.96 | 5.59 | 8.34 | 9.38 |
| CF (%) | 4.25 | 6.6 | 8.03 | 9.46 | 10.95 | 12.82 | 14.37 |
| DM (%) | 87.15 | 87.74 | 88.34 | 89.32 | 89.78 | 90.54 | 90.59 |

Note:
GE: gross energy; NDF: neutral detergent fiber, ADF: acid detergent fiber, ADL: acid detergent lignin; CF: crude fiber.

(4) Indicator Measurement

The fecal samples were collected, dried in an oven at 65° C. for 48 hours, weighed, crushed and passed through a 40-mesh sieve, and stored at −20° C. for analysis of various indicators. A combustion method was used to determine the energy in diet and feces (IKAC200, Germany), and a hydrolysis method was used to determine the amino acids in diet and feces (Biochrom30+, US).

Acid hydrolysis method: about 30-50 mg of sample to the nearest 0.1 mg was weighed and placed in a labeled polytetrachloroethylene tube with a cap. 10 ml of 6MHCl-phenol solution was added and then nitrogen was introduced to expel the air thoroughly. The glass tube was placed in a 110° C. oven and boiled for 24 hours, and filtration was performed after cooling. 1 ml of filtrate was drawn and evaporated to dryness in a crucible, the evaporated to dryness was repeated 2 times, residue in the crucible was transferred to a 25 ml volumetric flask, the solvent was added up to volume, AA was to be measured.

Oxidative hydrolysis method: 2.5 ml of peroxyformic acid was added to a test tube with a cap containing 30-50 mg of sample. The test tube was placed in an ice bath and oxidized for 16 hours. After the reaction, 0.25 g of sodium metabisulfite was added to each tube to decompose peroxyformic acid. Then 10 ml of 8 mol/L HCl (making the HCl concentration in the digestion solution 6 mol/L) was added, and digestion was conducted in an oven at 110° C. for 24 hours. Filtration followed after cooling. 1 ml of filtrate was drawn and evaporated to dryness in a crucible, the evaporation to dryness was repeated 2 times, residue in the crucible was transferred to a 25 ml volumetric flask, the solvent was added up to volume, AA was to be measured.

Alkaline hydrolysis method: 50 mg of the sample was accurately weighed and placed in a polytetrachloroethylene tube with a lid, and a hydrolysis reagent of bariumhydroxide (prepared before use) was added. Nitrogen was introduced to expel the air thoroughly, 5 ml of hydrolysis solution was added such that the sample on the tube wall was immersed in the hydrolysis solution, and the lid was screwed tightly. The test tube was placed in a 110° C. oven to hydrolyze for 24 hours, the hydrolysis solution was transferred to a 50 ml volumetric flask, the hydrolysis tube was rinsed with a small amount of re-distilled water by multiple times and transferred to a volumetric flask and made up to volume, and the volumetric flask was placed in an ice-water bath. The pH was adjusted to neutral with 6 mol/L HCl, the solution was shaken and filtered after being brought up to volume, and the supernatant was taken for testing for AA.

(5) Data Processing and Statistical Analysis

1) The calculation method of apparent metabolizable energy and true metabolizable energy of goose is determined by the metabolic test method.

$$\text{apparent metabolizable energy} = \frac{\text{gross energy of diet} - \text{fecal energy}}{\text{mass of diet}} \quad \text{formula A}$$

wherein the unit of apparent metabolizable energy is MJ/kg;

$$\text{true metabolizable energy} = \frac{\text{gross energy of diet} - \text{fecal energy} + \text{endogenous fecal energy}}{\text{mass of diet}} \quad \text{formula B}$$

wherein the unit of true metabolizable energy is MJ/kg.

2) Statistical Analysis

Completely randomized test data were analyzed using the GLM module of SAS software (SAS Institute, 2000). When the difference was significant, Duncan multiple comparisons were used. When $P<0.05$, the difference is significant, and the results are expressed as mean±standard deviation.

2. Results and Analysis (1) Effect of Fiber Level in Diet and Cecum on AME and TME 1) Effect of Fiber Level in Diet on AME and TME As shown in Table 10, the test in a AME and TME in group H in TEST 1 have a minimum value (11.58 and 13.72 KJ/kg, repsectivley), while AME and TME in group L and group M have an insignificant difference between the two groups, the difference of AME between group H and group M is up to 1.51 MJ/kg, and the difference of TME is up to 1.38 MJ/kg. As shown in Table 11, with the increase of fiber level in TEST 2, AME first increased and then decreased. There were maximum and minimum values in treatment group 3 and treatment group 7, and the difference was significant (P<0.01).

Taking into account the results of the two metabolizable energy experiments of neutralization, it is showed that as the fiber level increased within a certain range, the metabolizable energy showed an upward trend but did not reach a significant level, but as the fiber level further increased, the metabolizable energy decreased significantly. The apparent dry matter utility rate decreased significantly with the increase of fiber level, and the difference was significant (P<0.01). The apparent dry matter digestibility has maximum and minimum values in treatment group 1 and treatment group 6, and the difference between treatment groups 6 and 7 is not significant. A simple correlation analysis was performed between fiber level and metabolizable energy (Table 11), the results showed that the correlation coefficients of NDF, ADF, ADL and CF with the AME of intact geese were −0.82, −0.84, −0.83, and −0.77, respectively. The correlation coefficients of NDF, ADF, NDF and CF with the AME of cecectomized geese are −0.85, −0.86, −0.85 and −0.81, respectively, indicating that a strongly negative correlation between AME and diet fiber level.

2) Effect of Cecum on AME and TME

In experiment 1, both the apparent metabolizable energy and true metabolizable energy in the intact group were significantly higher than those of the cecectomized group (P<0.01), and the difference is 0.73 MJ/kg and 0.62 MJ/kg, respectively. In experiment 2, the apparent metabolizable energy of the intact group is also significantly higher than that in the cecectomized group, with a difference of 0.58 MJ/kg. The results of the two experiments showed that the nutrients in the diet can be utilized by the cecum, but the cecum has a limited utility rate of the diet's metabolizable energy.

TABLE 10

Effect of diet fiber level and cecum on AME and TME (on dry matter basis, MJ/kg)

| Item | Fiber level | Apparent metabolizable energy AME | True metabolizable energy TME |
|---|---|---|---|
| Cecectomized | L | 12.37 ± 0.70 | 14.67 ± 0.74 |
|  | M | 12.55 ± 0.52 | 14.59 ± 0.49 |
|  | H | 11.35 ± 0.33 | 13.63 ± 0.73 |
| Intact | L | 13.18 ± 0.53 | 15.29 ± 0.42 |
|  | M | 13.55 ± 0.89 | 15.53 ± 0.85 |
|  | H | 11.77 ± 0.70 | 13.81 ± 0.66 |
| Main effect |  |  |  |
| Cecal treatment |  |  |  |
| Cecectomized |  | 12.09 ± 0.74$^b$ | 14.29 ± 0.79$^b$ |
| Intact |  | 12.82 ± 1.05$^a$ | 14.91 ± 1.00$^a$ |
| Fiber level |  |  |  |
| L |  | 12.77 ± 0.72$^a$ | 14.98 ± 0.66$^a$ |
| M |  | 13.09 ± 0.88$^a$ | 15.10 ± 0.84$^a$ |
| H |  | 11.58 ± 0.58$^b$ | 13.72 ± 0.67$^b$ |
| P value |  |  |  |
| Cecum |  | 0.001 | 0.013 |
| Fiber level |  | <0.001 | <0.001 |
| Fiber × Cecum |  | 0.529 | 0.382 |

Under the same conditions, the values, accompanying lower case letters in the superscript or undenoted, in the same column indicate insignificant difference (P>0.05).

TABLE 11

Simple correlation between the apparent metabolizable energy and dry matter digestibility in cecectomized goose and in intact geese and the diet composition

|  | GE | DM | NDF | ADL | CF | AMEI | ADDMI | ADDMC | AMEC |
|---|---|---|---|---|---|---|---|---|---|
| DM | 0.98** |  |  |  |  |  |  |  |  |
| NDF | 0.99** | 0.98** |  |  |  |  |  |  |  |
| ADF | 0.99** | 0.98** | 1.00** |  |  |  |  |  |  |
| ADL | 0.99** | 0.98** | 1.00** |  |  |  |  |  |  |
| CF | 1.00** | 0.98** | 0.98** | 0.99** |  |  |  |  |  |
| AMEI | −0.80* | −0.81* | −0.82* | −0.83* | −0.77* |  |  |  |  |
| ADDMI | −0.97** | −0.99** | −0.97** | −0.98** | −0.97** | 0.87* |  |  |  |
| ADDMC | −0.95** | −0.99** | −0.95** | −0.96** | −0.96** | 0.85* | 1.00** |  |  |
| AMEC | −0.82* | −0.87* | −0.85* | −0.85* | −0.81* | 0.96** | 0.90** | 0.90** |  |
| AMEI-AMEC | −0.07 | −0.73 | −0.76* | −0.77* | −0.71 | 0.98** | 0.80* | 0.76* | 0.89** |

Note:
AMEI: apparent metabolizable energy in intact geese; ADDMI: apparent digestibility of dry matter in intact geese; AMEC: apparent metabolizable energy in cecectomized geese; ADDMC: apparent digestibility of dry matter in cecectomized geese.
*P < 0.05;
**P < 0.01.

Simple correlation analysis of metabolizable energy, dry matter digestibility and diet fiber composition shows that (Table 11) the metabolizable energy of cecectomized and intact geese are linearly correlated with CF, ADF, NDF, and ADL, and the correlation is high. The dry matter utility rate both in cecectomized goose and in intact geese are significantly negatively correlated with gross energy, dry matter content, CF, ADF, NDF and ADL. The reason may be that with the increase of fiber level, under the premise of unchanged metabolizable energy, the gross energy increases, but the corresponding fiber digestibility does not increase, resulting in a decrease in dry matter utility rate.

In this test, the metabolizable energy first increased and then decreased with the increase of fiber level. The Simple correlation between the levels of ADF, NDF, ADL and metabolizable energy was higher than that of CF. The linear regression equation and the quadratic curve regression equation of metabolizable energy with fiber as an independent variable are shown in Table 12. In the regression curves of CF against the metabolizable energy in intact geese, the metabolizable energy in cecectomized geese, and the difference between the two, the quadratic curve has high $R^2$ value than that for the linear curve, and the quadratic curve (table 12) of CF against the AMEI-AMEC value has higher $R^2$ than of ADF, NDF, the ADL, and P value is less than 0.05, indicating that the quadratic curve is statistically significant.

TABLE 12

Regression equation between metabolizable energy and cellulose level

| Independent variable | Regression equation | Goodness of fit $R^2$ |
|---|---|---|
| Straight line | | |
| AMEI-AMEC | $=-0.089* CF + 1.476$ | 0.491 ($P > 0.05$) |
| AMEI | $=0.167* CF + 14.57$ | 0.590 ($P < 0.05$) |
| AMEC | $=-0.078* CF + 13.09$ | 0.647 ($P < 0.05$) |
| Quadratic curve | | |
| AMEI-AMEC | $=-0.020* CF^2 + 0.333* CF - 0.476$ | 0.782 ($P < 0.05$) |
| AMEI | $=-0.024* CF^2 - 85* CF + 576.6$ | 0.733 ($P < 0.05$) |
| AMEC | $=-0.004* CF^2 + 0.341* CF + 12.21$ | 0.668 ($P < 0.05$) |
| AMEI-AMEC | $=-0.002*NDF^2 + 0.097*NDF - 0.128$ | 0.705 ($P < 0.05$) |
| AMEI-AMEC | $=-0.003*ADF^{2+0.074}*ADF + 0.483$ | 0.723 ($P < 0.05$) |
| AMEI-AMEC | $=-0.018* ADL^2 + 0.107* ADL + 0.700$ | 0.728 ($P < 0.05$) |

Note:
The fiber level s in the regression curve between AMEI-AMEC and CF, ADF, NDF, ADL is calculated on a dry matter basis.

TABLE 13

Effect of diet fiber level and cecum on digestibility of CF, NDF, ADF and ADL in geese (on dry matter basis, %)

| Item | fiber level | CF | NDF | ADF | ADL |
|---|---|---|---|---|---|
| Cecectomized | L | 45.09 ± 2.58 | 35.48 ± 3.40 | 18.00 ± 1.41 | 21.56 ± 2.39 |
|  | M | 50.54 ± 3.70 | 31.20 ± 3.16 | 18.44 ± 2.29 | 31.5 ± 3.02 |
|  | H | 48.40 ± 1.87 | 31.33 ± 2.57 | 21.42 ± 2.54 | 30.86 ± 3.08 |
| Intact | L | 38.27 ± 4.59 | 29.01 ± 2.34 | 22.18 ± 3.85 | 21.61 ± 1.22 |
|  | M | 47.47 ± 3.53 | 32.02 ± 2.12 | 23.66 ± 2.95 | 30.40 ± 2.36 |
|  | H | 51.36 ± 4.35 | 31.33 ± 3.61 | 23.13 ± 3.18 | 32.67 ± 1.53 |
| Main effect Cecal Treatment | | | | | |
| Cecectomized | | 48.19 ± 3.41 | 32.44 ± 3.43 | 19.40 ± 2.59$^b$ | 28.12 ± 5.33 |
| Intact | | 45.61 ± 7.00 | 30.69 ± 2.92 | 23.03 ± 3.2$^a$ | 28.22 ± 5.17 |
| Fiber level | | | | | |
| L | | 41.11 ± 5.12$^b$ | 31.71 ± 4.28 | 20.09 ± 3.52 | 21.58 ± 1.77$^b$ |
| M | | 49.00 ± 3.80$^a$ | 31.61 ± 2.60 | 21.25 ± 3.72 | 30.91 ± 2.63$^a$ |
| H | | 49.88 ± 3.56$^a$ | 31.33 ± 2.96 | 22.21 ± 2.87 | 31.76 ± 2.52$^a$ |
| P value | | | | | |
| Cecum | | 0.0591 | 0.0567 | 0.0003 | 0.7371 |
| Fiber level | | <0.0001 | 0.7278 | 0.1659 | <0.0001 |
| Fiber × Cecum | | 0.0060 | 0.0077 | 0.2793 | 0.2817 |

Note:
Under the same conditions, the values, accompanying lowercase letters in the superscript or undenoted, in the AME column indicate insignificant difference ($P > 0.05$).

Example 3

1. Materials and Methods (1) Test Diet 9 kinds of rice (numbered 1-9), 5 kinds of wheat (numbered 10-14) and 5 kinds of corn (numbered 15-19) from different regions, and their nutritional components are shown in Table 14.

(2) Measurement Test of Biological Metabolizable Energy of Goose Feed and Test Design In this experiment, the simulative digestion the gross energy technique and the emptying forced feeding technique was used to determine the metabolizable energy values of 19 goose energy feed samples.

35 healthy adult black male geese (average weight 4.1 kg) were selected and divided into 5 groups with 7 replicates in each group, and raised in a single cage in AME tabolic cage. The geese were left to intake food and drink freely, with an illumination time of being 16 h. Feeding management was conducted by referring to the routine feeding management procedures of South China Agricultural University (Animal Feed Science and Technology, 2017, 236: 115-121). The emptying forced feeding technique included three days of the pre-feeding period. The geese were fasted for 24 hours before force-feeding, and left to drink water freely throughout the test period. 60 g air-dried test material was precisely fed, fecal samples within 48 h were collected, and the endogenous feces within 48 hours were collected using a starvation method. A recovery period of 7-10 days was set after each test.

(3) Simulative Digestion Test and Test Design

The simulative digestion program was set by referring to the data in subsection "(4) Steps of simulative digestion" in section "1. Materials and methods" in Example 1.

(4) Indicator Measurement

The fecal samples were collected in the emptying forced feeding technique, dried in an oven at 65° C. for 48 hours, weighed, crushed and passed through a 40-mesh sieve, and stored at −20° C. for further measurement of dry matter digestibility, metabolizable energy utility rate and metabolizable energy values.

In the simulative digestion gross energy technique, the simulative dry matter digestibility, simulative energy digestibility, and value of simulative digestion gross energy of 19 feed ingredient samples were measured.

TABLE 14

Nutrient content of rice, wheat and corn from different producing areas (on dry matter basis, %)

| No. | Origin | GE | CF | NDF | ADF | ADL | CP | Ash | DM |
|---|---|---|---|---|---|---|---|---|---|
| 1 | Guangxi | 17.54 | 10.35 | 23.35 | 15.88 | 5.26 | 7.07 | 3.93 | 89.72 |
| 2 | Hainan | 17.91 | 13.05 | 21.58 | 14.41 | 4.08 | 7.31 | 5.48 | 88.04 |
| 3 | Henan | 18.33 | 10.87 | 29.18 | 11.62 | 3.55 | 8.74 | 3.54 | 86.24 |
| 4 | Hubei | 17.69 | 11.09 | 24.09 | 14.44 | 5.29 | 6.64 | 5.95 | 87.89 |
| 5 | Liaoning | 18.27 | 9.82 | 24.35 | 11.58 | 3.55 | 8.13 | 3.31 | 86.79 |
| 6 | Heilongjiang | 17.87 | 9.18 | 20.27 | 10.36 | 3.22 | 8.31 | 3.51 | 85.79 |
| 7 | Guangdong | 18.37 | 11.07 | 36.21 | 15.54 | 6.53 | 6.54 | 4.51 | 87.09 |
| 8 | Hebei | 18.20 | 11.81 | 35.95 | 14.86 | 5.77 | 6.99 | 5.82 | 88.53 |
| 9 | Sichuan | 17.77 | 11.86 | 41.55 | 13.35 | 5.08 | 7.90 | 4.15 | 89.43 |
| 10 | Shanxi | 17.52 | 1.73 | 43.37 | 3.21 | 0.62 | 13.81 | 1.48 | 89.38 |
| 11 | Henan | 18.09 | 1.96 | 29.17 | 2.60 | 0.35 | 16.97 | 1.73 | 89.76 |
| 12 | Gansu | 17.92 | 1.73 | 25.18 | 2.86 | 0.45 | 15.88 | 2.00 | 91.62 |
| 13 | Anhui | 17.67 | 1.66 | 23.37 | 2.88 | 0.56 | 15.01 | 1.92 | 89.94 |
| 14 | Hebei | 17.34 | 1.82 | 9.76 | 2.80 | 0.40 | 16.06 | 2.45 | 91.38 |
| 15 | Heilongjiang | 18.63 | 2.14 | 12.91 | 3.78 | 0.42 | 10.22 | 1.98 | 90.23 |
| 16 | Henan | 18.09 | 1.28 | 9.40 | 1.94 | — | 9.81 | 1.56 | 85.53 |
| 17 | Anhui | 17.44 | 1.44 | 9.41 | 2.36 | 0.08 | 9.80 | 1.86 | 87.38 |
| 18 | Shanxi | 19.09 | 1.08 | 7.36 | 1.97 | 0.03 | 9.91 | 1.08 | 87.09 |
| 19 | Hebei | 20.07 | 1.36 | 7.87 | 1.95 | — | 9.61 | 1.46 | 86.62 |

Note:
No. 1-19 are all energy feeds, wherein No. 1-9 for rice from different producing areas, 10-14 for wheat from different producing areas, and 15-19 for corn from different producing areas.

(5) Data Processing and Statistical Analysis

Variance analysis was performed on the completely randomized test data that were analyzed using the GLM module of SAS software. When the difference was significant, Duncan multiple comparisons are used. Correlation analysis was performed between the simulative digestion gross energy technique and the biological method by using the PROCCORR module of SAS, and GLM module of by SAS was used to establish a linear equation and a non-linear regression equation. When P<0.05, the difference was significant.

$$\text{rectified value of simulative digestion of gross energy (SDGE1) (MJ/Kg)} = \text{SDGE} + 0.74 \quad \text{formula F:}$$

$$\text{simulative digestion of gross energy} = -0.020 \ast CF2 + 0.333 \ast CF - 0.476 + \text{SDGE} \quad \text{formula E:}$$

[1] Obtained through the correction of SDGE by using an average value 0.74 MJ/kg of the change of energy values in the cecum, the average value 0.74 MJ/kg being obtained via the difference between the metabolizable energy in the cecectomized geese and in the intact geese at an appropriate level in Example 2.

[2] Obtained through the correction of SDGE by using a regression curve for the change of energy values in the cecum, the regression curve being obtained CF levels.

2. Results (1) Comparison of Dry Matter Utility Rates and Metabolizable Energy Values of 19 Energy Feed Samples Measured by Simulative Digestion Gross Energy Technique and by Biological Method.

From the comparison of the metabolizable energy by a biological method with the simulative digestion gross energy technique SDGE of 19 samples (Table 15), the TME values of the 9 rice samples are significantly higher than the SDGE, with the difference in the range of 2.52-4.23 MJ/kg. Among them, the AME values of 5 rice samples are significantly higher than the SDGE value, and the AME values of 4 rice samples are not significantly different from SDGE, with the difference in a range of 0.40-2.11 MJ/kg. The TME values of wheat are all higher than SDGE, with the difference in a range of 0.94-1.47 MJ/kg. AME values are all lower than SDGE, and AEM values of 3 wheat samples are significantly lower than SDGE, AME values of 2 samples are not significantly different from SDGE, with the difference in a range of −1.11-0.63 MJ/kg. TME of corn significantly is higher than the SDGE value, with a difference of 1.72-2.96 MJ/kg. The difference between AME value and SDGE is in the range of −0.12-1.08 MJ/kg, except for the No. 16 sample in which the difference between the AME value and SDGE is not significant.

TABLE 15

Comparison of energy values of 19 goose energy feeds in biological method and in simulative digestion gross energy technique (on dry matter basis)

| Feed Number | Biological method | | | | Simulative digestion gross energy technique | | Difference | |
|---|---|---|---|---|---|---|---|---|
| | AME (MJ/kg) | CV (%) | TME (MJ/kg) | CV (%) | SDGE (MJ/kg) | CV (%) | AME - SDGE (MJ/kg) | TME - SDGE (MJ/kg) |
| 1 | 13.58[b] | 3.82 | 15.63[a] | 3.31 | 11.57[c] | 1.54 | 2.01 | 4.06 |
| 2 | 12.78[b] | 5.48 | 14.85[a] | 4.69 | 11.93[b] | 0.44 | 0.85 | 2.92 |
| 3 | 13.07[b] | 4.13 | 15.19[a] | 3.57 | 12.67[b] | 0.96 | 0.40 | 2.52 |
| 4 | 13.20[b] | 4.69 | 15.29[a] | 4.05 | 12.37[c] | 0.70 | 0.83 | 2.92 |
| 5 | 13.95[b] | 4.98 | 16.06[a] | 4.32 | 12.91[c] | 1.19 | 1.04 | 3.15 |
| 6 | 13.12[b] | 2.66 | 15.25[a] | 2.27 | 12.54[b] | 1.06 | 0.58 | 2.71 |
| 7 | 13.89[b] | 7.29 | 16.01[a] | 6.32 | 11.78[c] | 0.59 | 2.11 | 4.23 |
| 8 | 13.40[b] | 7.00 | 15.48[a] | 6.06 | 11.78[c] | 1.51 | 1.62 | 3.70 |
| 9 | 12.48[b] | 4.50 | 14.47[a] | 3.24 | 11.69[b] | 0.69 | 0.79 | 2.78 |
| 10 | 12.52[c] | 2.99 | 14.59[a] | 2.57 | 13.58[b] | 0.97 | −1.06 | 1.01 |
| 11 | 12.12[b] | 3.13 | 14.22[a] | 2.67 | 12.75[b] | 1.54 | −0.63 | 1.47 |
| 12 | 12.59[c] | 4.52 | 14.60[a] | 3.89 | 13.61[b] | 0.39 | −1.02 | 0.99 |
| 13 | 12.62[c] | 4.56 | 14.67[a] | 3.92 | 13.73[b] | 1.41 | −1.11 | 0.94 |
| 14 | 12.12[b] | 3.02 | 14.14[a] | 2.59 | 12.99[b] | 0.50 | −0.87 | 1.15 |
| 15 | 14.13[b] | 5.51 | 15.99[a] | 0.79 | 14.09[b] | 1.18 | 0.04 | 1.90 |
| 16 | 14.02[b] | 3.41 | 15.90[a] | 0.48 | 12.94[c] | 0.16 | 1.08 | 2.96 |
| 17 | 13.55[b] | 4.16 | 15.41[a] | 0.56 | 12.89[b] | 1.40 | 0.66 | 2.52 |
| 18 | 14.94[b] | 2.09 | 16.98[a] | 0.64 | 14.75[b] | 0.08 | 0.19 | 2.23 |
| 19 | 16.09[b] | 4.36 | 17.93[a] | 0.70 | 16.21[b] | 1.55 | −0.12 | 1.72 |

Standard Deviation = |SDGE-ME|/ME-

Note:
the values, accompanying lowercase letters in the superscript or undenoted, in the same row indicate insignificant difference (P > 0.05).

TABLE 16

Comparison of metabolizable energy values and rectified value of simulative digestion gross energy for 19 goose energy feeds (on dry matter basis)

| Diet No. | Biological Method | | SDGE Technique | | | Estimated Deviation of SDGE | | Estimated Deviation of SDGE1 | | Estimated Deviation of SDGE2 | |
|---|---|---|---|---|---|---|---|---|---|---|---|
| | AME (MJ/kg) | TME (MJ/kg) | SDGE (MJ/kg) | SDGE1 (MJ/kg) | SDGE2 (MJ/kg) | (%) | (%) | (%) | (%) | (%) | (%) |
| 1 | 13.58 | 15.63 | 11.57 | 12.31 | 12.40 | 14.80 | 25.98 | 9.35 | 21.24 | 8.70 | 20.68 |
| 2 | 12.78 | 14.85 | 11.93 | 12.67 | 12.39 | 6.65 | 19.66 | 0.86 | 14.68 | 3.02 | 16.54 |
| 3 | 13.07 | 15.19 | 12.67 | 13.41 | 13.45 | 3.06 | 16.59 | 2.60 | 11.72 | 2.91 | 11.45 |
| 4 | 13.2 | 15.29 | 12.37 | 13.11 | 13.13 | 6.29 | 19.10 | 0.68 | 14.26 | 0.55 | 14.15 |
| 5 | 13.95 | 16.06 | 12.91 | 13.65 | 13.78 | 7.46 | 19.61 | 2.15 | 15.01 | 1.25 | 14.23 |
| 6 | 13.12 | 15.25 | 12.54 | 13.28 | 13.44 | 4.42 | 17.77 | 1.22 | 12.92 | 2.40 | 11.90 |
| 7 | 13.89 | 16.01 | 11.78 | 12.52 | 12.54 | 15.19 | 26.42 | 9.86 | 21.80 | 9.72 | 21.68 |
| 8 | 13.4 | 15.48 | 11.78 | 12.52 | 12.45 | 12.09 | 23.90 | 6.57 | 19.12 | 7.11 | 19.59 |
| 9 | 12.48 | 14.47 | 11.69 | 12.43 | 12.35 | 6.33 | 19.21 | 0.40 | 14.10 | 1.04 | 14.65 |
| 10 | 12.52 | 14.59 | 13.58 | 14.32 | 13.62 | 8.47 | 6.92 | 14.38 | 1.85 | 8.79 | 6.65 |
| 11 | 12.12 | 14.22 | 12.75 | 13.49 | 12.85 | 5.20 | 10.34 | 11.30 | 5.13 | 6.02 | 9.64 |
| 12 | 12.59 | 14.6 | 13.61 | 14.35 | 13.65 | 8.10 | 6.78 | 13.98 | 1.71 | 8.42 | 6.51 |
| 13 | 12.62 | 14.67 | 13.73 | 14.47 | 12.75 | 8.80 | 6.41 | 14.66 | 1.36 | 8.97 | 6.26 |
| 14 | 12.12 | 14.14 | 12.99 | 13.73 | 13.05 | 7.18 | 8.13 | 13.28 | 2.90 | 7.70 | 7.68 |
| 15 | 14.13 | 15.99 | 14.09 | 14.83 | 14.24 | 0.28 | 11.88 | 4.95 | 7.25 | 0.74 | 10.98 |
| 16 | 14.02 | 15.9 | 12.94 | 13.68 | 12.86 | 7.70 | 18.62 | 2.43 | 13.96 | 8.29 | 19.14 |
| 17 | 13.55 | 15.41 | 12.89 | 13.63 | 12.85 | 4.87 | 16.35 | 0.59 | 11.55 | 5.15 | 16.60 |
| 18 | 14.94 | 16.98 | 14.75 | 15.49 | 14.61 | 1.27 | 13.13 | 3.68 | 8.78 | 2.21 | 13.96 |
| 19 | 16.09 | 17.93 | 16.21 | 16.95 | 16.15 | 0.75 | 9.59 | 5.34 | 5.47 | 0.37 | 9.93 |

The estimated deviations of SDGE and metabolizable energy are shown in Table 16. The estimated deviations of SDGE and its rectified values with respect to AME of the rice are 3.06-15.19% for SDGE, 0.40-9.86% for SDGE 1, 0.55-9.72% for SDGE 2, respectively, while the range of estimated deviation with respect to the TME exceeds 10%. The range for the estimated deviation of SDGE and its rectified value with respect to AME of wheat are 5.20-8.80% for SDGE, 11.30-14.66% for SDGE 1, 6.02-8.97% for SDGE 2, while the estimated deviation of TME with respect to the TME is 6.41-10.34% for SDGE, 1.36-5.13% for SDGE 1, 6.26-9.64% for SDGE 2. The range for estimated deviation of SDGE and its rectified value with respect to AME of the corn is 0.28-7.70% for SDGE, 0.59-4.95% for SDGE 1, 0.37-8.29% for SDGE 2, and the estimated deviation with respect to TME is 9.59-18.62%, 5.47-13.96%, SDGE 29.93-19.14%, respectively.

Figure 3:
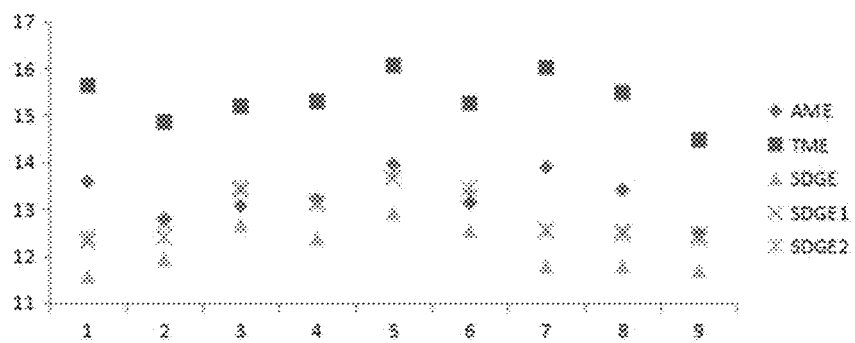
FIG. 3 shows the values of AME, TME, SDGE, SDGE 1 and SDGE 2 of 9 rice samples.
Figure 4:
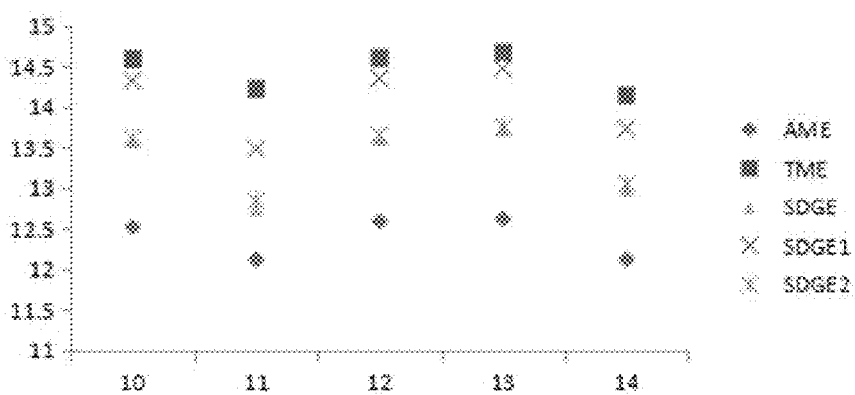
FIG. 4 shows the values of AME, TME, SDGE, SDGE 1 and SDGE 2 of 5 wheat samples.
Figure 5:
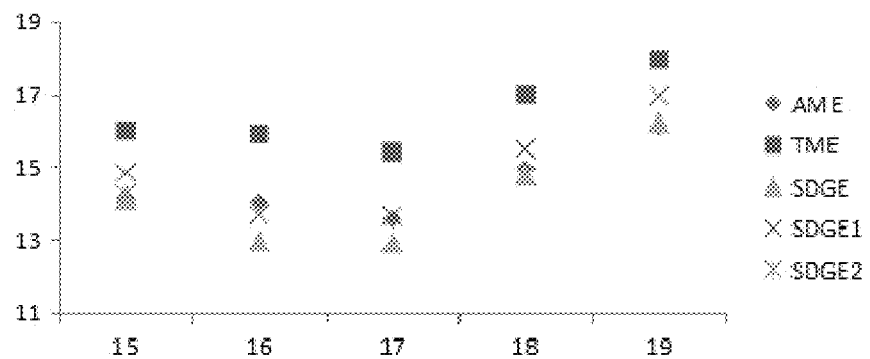
FIG. 5 shows the values of AME, TME, SDGE, SDGE 1 and SDGE 2 of 5 corn samples.

The TME value of rice is higher than other energy values (FIG. 3), the SDGE value by the simulative digestion gross energy technique is smaller than other energy values, and the rectified values SDGE 1 and SDGE 2 by the simulative digestion gross energy technique overlap with the AME value. The TME value of wheat is higher than other energy values (FIG. 4), and SDGE, SDGE 1 and SDGE 2 values by the simulative digestion gross energy technique are all in the range between AME and TME, without overlap with a ME or TME. The AME corn by emptying forced feeding technique overlaps with the values SDGE and SDGE 2 by simulative digestion gross energy technique but does not overlap with SDGE 1 (FIG. 5).

On the whole, except for rice samples Nos. 1, 7 and 8, the AME value and SDGE value of other 16 samples are all below 10%, which meets the accuracy requirements of the biological method for metabolizable energy. After rectifying the portion, utilized by the cecum, of the metabolizable energy value, within a range of appropriate fiber levels via the value of simulative digestion gross energy technique, it is found that, except for all 5 wheat samples, the estimated deviations of the rectified value SDGE 1 by simulative digestion gross energy technique 9 rice samples and 5 corn samples with respect to the AME are all below 10%. However, after rectifying the value simulative digestion gross energy technique by the regression curve created by using the fiber level and the in-cecum metabolizable energy value, it is found that the estimated deviations of rectified values SDGE 2 of all 19 samples by simulative digestion gross energy technique with respect to the AME are below 10%, but the estimated deviations of SDGE with respect to TME are relatively large. The digestive enzymes in the simulative digestion gross energy technique are only composed protease and amylase, which are not as abundant in species as the intestinal enzymes in the biological method, lacking the peptidase secreted by the intestinal mucosa or peptidase secreted by the pancreas, etc. leading to a big difference between the SDGE value and the TME value.

TABLE 17

Proportion of coefficient of variations in respective intervals for energy value and dry matter digestibility of 19 samples by simulative digestion gross energy technique and by biological method

| Coefficient of variation | Biological method | | | Simulative digestion gross energy technique | | |
| --- | --- | --- | --- | --- | --- | --- |
| | ADDM | AME | ADGE | SDDM | SDGE | SYGE |
| 1.0% or less | 0 | 0 | 0 | 63.16% (12) | 52.63% (10) | 52.63% (10) |
| 1.0-2.5% | 5.26% (1) | 5.26% (1) | 5.26% (1) | 31.58% (6) | 47.37% (9) | 47.37% (9) |
| 2.5-5.0% | 73.68% (14) | 84.21% (16) | 78.95% (15) | 5.26% (1) | | |
| 5.0-7.5% | 15.79% (3) | 10.53% (2) | 15.79% (3) | | | |
| 7.5% or more | 5.26% (1) | | | | | |

TABLE 18

Simple correlation coefficient between the value of simulative digestion gross energy of rice and the metabolizable energy of biological method as well as raw material composition

| Item | AME | TME | ADDM | SDGE | SDGE 1 | SDGE 2 | SDDM |
| --- | --- | --- | --- | --- | --- | --- | --- |
| TME | 1.00** | | | | | | |
| ADDM | 0.63 | 0.62 | | | | | |
| SDGE | 0.20 | 0.23 | 0.11 | | | | |
| SDGE 1 | 0.20 | 0.23 | 0.11 | 1.00** | | | |
| SDGE 2 | 0.14 | 0.17 | 0.08 | 0.99** | 0.99** | | |
| SDDM | −0.04 | −0.02 | 0.30 | 0.81** | 0.81** | 0.82** | |
| GE | 0.42 | 0.45 | −0.36 | 0.37 | 0.37 | 0.34 | −0.12 |
| CF | −0.02 | −0.06 | −0.09 | −0.85** | −0.85** | −0.91** | −0.79* |
| NDF | −0.17 | −0.17 | −0.52 | −0.47 | −0.47 | −0.41 | −0.53 |
| ADF | 0.17 | 0.13 | 0.10 | −0.81** | −0.81** | −0.86** | −0.83** |
| ADL | 0.23 | 0.20 | 0.01 | −0.75* | −0.75* | −0.74* | −0.82** |
| CP | −0.30 | −0.27 | −0.18 | 0.62 | 0.62 | 0.65 | 0.72* |
| DM | −0.25 | −0.30 | 0.04 | −0.80** | −0.80** | −0.78* | −0.52 |

Note:
*$P < 0.05$,
**$P < 0.01$

From the comparison of the measuring accuracy for 19 feed samples determined by the two methods (Table 17), the coefficient of variation of AME and ADGE determined by the biological method are all less than or equal to 7.5% but are all higher than 1.0%. Among them, the coefficients variation of AME and ADGE are mainly concentrated between 2.5% and 5.0%, with in this range, AME accounts for 84.21% and ADGE accounts for 78.95%.

Coefficients of variation for SDGE and SYGE determined by simulative digestion gross energy technique are less than or equal to 2.5%. Among them, coefficients of variation of SDGE and SYGE for 10 samples are less than or equal to 1.0%, accounting for 52.63% of the total number of samples. The coefficient of variation of SDDM is less than or equal to 5.0%, among them the coefficient of variation of 12 samples is less than or equal to 1.0%, accounting for 63.16% of the total number of samples.

TABLE 19

Simple correlation coefficient between the value simulative digestion gross energy of wheat and the metabolizable energy of biological method as well as raw material composition

| Item | AME | TME | SDGE | SDGE 1 | SDGE 2 |
|---|---|---|---|---|---|
| TME | 0.99** | | | | |
| SDGE | 0.98** | 0.95* | | | |
| SDGE 1 | 0.98** | 0.95* | 1.00** | | |
| SDGE 2 | 0.98** | 0.95* | 1.00** | 1.00** | |
| GE | 0.02 | 0.08 | −0.19 | −0.19 | −0.19 |
| CF | −0.89* | −0.84 | −0.96** | −0.96** | −0.96** |
| NDF | 0.41 | 0.51 | 0.32 | 0.32 | 0.32 |
| ADF | 0.61 | 0.61 | 0.70 | 0.70 | 0.70 |
| ADL | 0.77 | 0.80 | 0.83 | 0.83 | 0.83 |
| CP | −0.67 | −0.68 | −0.75 | −0.75 | −0.75 |
| DM | −0.08 | −0.22 | −0.03 | −0.03 | −0.03 |

Note:
*$P < 0.05$,
**$P < 0.01$.

As shown in Table 18, Table 19 and Table 20, the SDGE values of wheat and corn are significantly correlated with a ME and TME, and the correlation coefficients are all above 0.90, indicating the extremely high correlation between SDGE of these two diets by simulative digestion gross energy technique and AME as well as TME determined by and emptying forced feeding technique. There is a significant negative correlation between CF and SDGE in rice, while there is no a significant correlation between CF and SDGE in corn. There is no significant correlation between GE of rice and wheat and AME, while the correlation between GE of Corn and AME is up to 0.97. There is no significant correlation between CF and GE of rice, wheat and corn.

TABLE 20

Simple correlation coefficient between the value of simulative digestion gross energy corn and the metabolizable energy biological method as well as raw material composition

| Item | AME | TME | SDGE | SDGE1 | SDGE2 |
|---|---|---|---|---|---|
| TME | 1.00** | | | | |
| SDGE | 0.97** | 0.96** | | | |
| SDGE1 | 0.97** | 0.96** | 1.00** | | |
| SDGE2 | 0.97** | 0.96** | 1.00** | 1.00** | |
| GE | 0.97** | 0.97** | 0.98** | 0.98** | 0.98** |
| CF | −0.29 | −0.33 | −0.10 | −0.10 | −0.10 |
| NDF | −0.54 | −0.57 | −0.38 | −0.38 | −0.38 |
| ADF | −0.37 | −0.39 | −0.15 | −0.15 | −0.15 |

TABLE 20-continued

Simple correlation coefficient between the value of simulative digestion gross energy corn and the metabolizable energy biological method as well as raw material composition

| Item | AME | TME | SDGE | SDGE1 | SDGE2 |
|---|---|---|---|---|---|
| CP | −0.48 | −0.46 | −0.30 | −0.30 | −0.30 |
| DM | −0.22 | −0.22 | 0.03 | 0.03 | 0.03 |

Note:
*$P < 0.05$,
**$P < 0.01$.

Example 4

1. Materials and Methods
(1) Test Diet

From the rice, wheat and corn samples obtained in Example 3, each of which was selected and mixed according to a certain ratio to prepare 4 kinds of diets. The ratio and nutritional components of the test diet are shown in Table 21. Furthermore, No. 1-4 diets in Test 2 in Example 3 and No. 5-9 diets in Example 1 were brought to match No. 1-9 compound feeds in this part of the test, and their SDGE values and AME values were compared.

TABLE 21

Composition and nutrient content of test diet (on dry matter basis, %)

| Item | A | B | C | D |
|---|---|---|---|---|
| Rice6 | 50 | 50 | — | 33.33 |
| Wheat2 | 50 | — | 50 | 33.33 |
| Corn5 | — | 50 | 50 | 33.33 |
| CF | 5.87 | 5.61 | 1.74 | 4.10 |
| NDF | 24.01 | 14.22 | 19.73 | 20.45 |
| ADF | 6.34 | 6.13 | 2.28 | 5.04 |
| ADL | 1.59 | 1.74 | — | 1.02 |
| CP | 12.72 | 8.99 | 13.37 | 11.62 |
| GE | 18.03 | 19.21 | 19.37 | 18.90 |

(2) Measurement Test and Test Design of the Biological Metabolizable Energy of Goose Feed
Refer to step (2) in Example 3.
(3) Simulative Digestion Test and Test Design
Refer to step (3) in Example 3
(4) Indicator Measurement
Refer to step (4) in Example 3
(5) Data processing and statistical analysis
The Experimental Data were Processed by Excel 2007.

2. Results and Analysis
(1) Comparison of the Additivity of Simulative Digestion Gross Energy Technique and Emptying Forced Feeding Technique to the Energy Value of Energy Feed As shown in Table 22, the difference between the measured value and the calculated value of AME for four kinds of diet is in the range of 0.31-0.56 MJ/kg, and the percentage of the measured value over the calculated value is 102.46-103.83%. There is a small difference between the measured value and the calculated value of SDGE, with the difference being in the range of 0.09-0.22 MJ/kg, and the percentage of the measured value over the calculated value is 100.71-101.59%. By comparing two of them, SDGE has a smaller difference between the measured value and calculated value than AME does, and the simulative digestion gross energy technique has better additivity than the emptying forced feeding technique.

TABLE 22

Comparison of additivity between the SDGE by simulative digestion gross energy technique and AME by emptying forced feeding technique for energy feed (on dry matter basis)

| Diet number | | A | B | C | D |
|---|---|---|---|---|---|
| Calculated value (MJ/kg) | AME | 12.62 | 14.61 | 14.11 | 13.78 |
| | SDGE | 12.65 | 14.38 | 14.48 | 13.83 |
| | SDGE1 | 13.39 | 15.12 | 15.22 | 14.57 |
| | SDGE2 | 13.44 | 15.14 | 14.52 | 14.38 |
| Measured value (MJ/kg) | AME | 12.93 | 15.17 | 14.55 | 14.28 |
| | SDGE | 12.74 | 14.57 | 14.66 | 14.05 |
| | SDGE1 | 13.48 | 15.31 | 15.40 | 14.79 |
| | SDGE2 | 13.53 | 15.33 | 14.70 | 14.60 |
| Measured value-calculated value (MJ/kg) | AME | 0.31 | 0.56 | 0.44 | 0.50 |
| | SDGE | 0.09 | 0.19 | 0.18 | 0.22 |
| Measured value/calculated value (%) | AME | 102.46 | 103.83 | 103.12 | 103.63 |
| | SDGE | 100.71 | 101.32 | 101.24 | 101.59 |

TABLE 23

Comparison of relative deviation between the SDGE by simulative digestion gross energy method and AME by emptying forced feeding technique for energy feed (on dry matter basis)

| Measured value | A | B | C | D |
|---|---|---|---|---|
| SDGE-AME (MJ/kg) | −0.19 | −0.60 | 0.11 | −0.23 |
| SDGE1-AME (MJ/kg) | 0.55 | 0.14 | 0.85 | 0.51 |
| SDGE2-AME (MJ/kg) | 0.60 | 0.16 | 0.15 | 0.32 |
| \|SDGE-AME\|/AME (%) | 1.47 | 3.96 | 0.76 | 1.61 |
| \|SDGE1-AME\|/AME (%) | 4.25 | 0.92 | 5.84 | 3.57 |
| \|SDGE2-AME\|/AME (%) | 4.43 | 1.04 | 1.02 | 2.19 |
| CV (%) | | | | |
| AME | 7.19 | 6.99 | 5.77 | 5.60 |
| SDGE | 0.71 | 1.37 | 0.48 | 0.36 |
| SDGE1 | 0.67 | 1.31 | 0.45 | 0.34 |
| SDGE2 | 0.67 | 1.30 | 0.48 | 0.34 |

Figure 6:
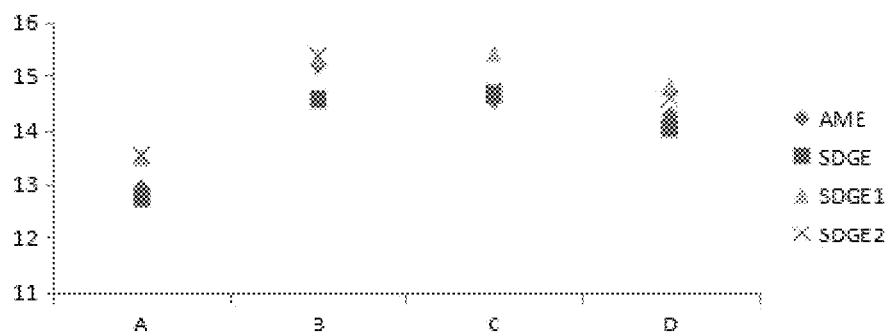
FIG. 6 shows the comparison of measured values of AME, the TME, SDGE, SDGE 1 and SDGE 2 for 4 energy formula feed.

As shown in Table 23, the range of difference between SDGE and AME is −0.60-0.11 MJ/kg, and the relative deviation is 0.76-3.96%. Among four compound feeds, there is an overlap between AME and SDGE, and SDGE 1 and SDGE 2 have higher values than AME (FIG. 6). The range of difference between SDGE 1 and AME is 0.14-0.85 MJ/kg, and the relative deviation is 0.92-5.84%. The range of difference between SDGE 2 and AME is 0.15-0.60 MJ/kg, and the relative deviation is 1.02-4.43. It can be seen from the comparison of different range and relative deviation that there is the biggest difference between SDGE and AME, and there is the smallest difference between SDGE 2 and AME; there a smallest relative deviation between SDGE and AME, and there is a biggest relative deviation between SDGE 1 and AME. It can be seen from the comparison between the accuracy of AME and of SDGE that the coefficient of variation of AME is in the range of 5.60-7.19%; the coefficient of variation of SDGE is 0.36-1.37%, and the accuracy of simulative digestion gross energy technique is higher than that of emptying forced feeding technique.

(2) Comparison of Additivity Between the Energy Value by Simulative Digestion Gross Energy Method and by Emptying Forced Feeding Technique for Complete Feed (on Dry Matter Basis)

TABLE 24

Comparison of additivity between the SDGE by simulative digestion gross energy technique and AME by emptying forced feeding technique for compound feed (on dry matter basis)

| Diet number | | 1 | 2 | 3 | 4 | 5 | 6 | 7 | 8 | 9 |
|---|---|---|---|---|---|---|---|---|---|---|
| calculated value (MJ/kg) | AME[1] | 12.05 | 12.13 | 12.36 | 11.81 | 12.14 | 12.01 | 12.88 | 12.76 | 12.76 |
| | SDGE[2] | 12.33 | 12.38 | 12.43 | 12.48 | 12.70 | 13.06 | 13.05 | 13.42 | 13.69 |
| | SDGE 1 | 13.07 | 13.12 | 13.17 | 13.22 | 13.44 | 13.80 | 13.79 | 14.16 | 14.43 |
| | SDGE 2 | 12.91 | 13.23 | 13.34 | 13.36 | 13.31 | 13.68 | 13.66 | 14.04 | 14.31 |
| measured value (MJ/kg) | AME | 13.02 | 13.76 | 13.96 | 12.51 | 12.80 | 12.96 | 13.25 | 13.44 | 13.40 |
| | SDGE | 12.84 | 12.88 | 12.95 | 12.95 | 12.88 | 12.95 | 13.48 | 13.32 | 13.64 |
| | SDGE 1 | 13.58 | 13.62 | 13.69 | 13.69 | 13.62 | 13.69 | 14.22 | 14.06 | 14.38 |
| | SDGE 2 | 13.42 | 13.73 | 13.86 | 13.83 | 13.49 | 13.56 | 14.09 | 13.93 | 14.25 |
| measured value-calculated value (MJ/kg) | AME | 0.97 | 1.63 | 1.60 | 0.70 | 0.66 | 0.95 | 0.37 | 0.68 | 0.64 |
| | SDGE | 0.51 | 0.50 | 0.52 | 0.47 | 0.18 | −0.11 | 0.43 | −0.10 | −0.05 |
| measured value/calculated value (%) | AME | 108.05 | 113.44 | 112.94 | 105.93 | 105.44 | 107.91 | 102.87 | 105.33 | 105.02 |
| | SDGE | 104.14 | 104.04 | 104.18 | 103.77 | 101.44 | 99.12 | 103.33 | 99.25 | 99.61 |

[1] In the calculated value of AME, the metabolizable energy of the energy feed was obtained by a direct forced feeding method, fat powder and starch were mixed at a ratio of 1:9 and then measured, and protein feed ingredients and starch were mixed at a ratio of 4:6 and measured.
[2] In the calculated value of SDGE, only SDGE value of the corn, soybean meal, rice husk, wheat bran, corn gluten meal and the fat powder was used, without calculating the SDGE values of the premix and the AA.

As shown in Table 24, the difference between the measured value and calculated value of AME for 9 kinds of diet is in the range of 0.37-1.63 MJ/kg, the percentage between the measured value and the calculated value is 102.87-113.44%. The difference between the measured value and the calculated value of SDGE is small, with the difference in the range of −0.05-0.52 MJ/kg, and the percentage of the measured value over the calculated value is 99.12-104.18%. The percentage of the measured value over the calculated value, and the range of difference in the simulative digestion gross energy technique are smaller than the emptying forced feeding technique, indicating that the simulative digestion gross energy technique additivity is better than the emptying forced feeding technique.

TABLE 25

Comparison of relative deviation between the SDGE by simulative digestion gross energy technique and AME by emptying forced feeding technique for nine compound feeds (on dry matter basis)

| Measured value | 1 | 2 | 3 | 4 | 5 | 6 | 7 | 8 | 9 |
|---|---|---|---|---|---|---|---|---|---|
| SDGE - AME (MJ/kg) | −0.18 | −0.88 | −1.01 | 0.44 | 0.08 | −0.01 | 0.23 | −0.12 | 0.24 |
| SDGE 1- AME (MJ/kg) | 0.56 | −0.14 | −0.27 | 1.18 | 0.82 | 0.73 | 0.97 | 0.62 | 0.98 |
| SDGE 2- AME (MJ/kg) | 0.40 | −0.03 | −0.10 | 1.32 | 0.69 | 0.60 | 0.84 | 0.49 | 0.85 |
| ISDGE - AMEI/AME (%) | 1.38 | 6.40 | 7.23 | 3.52 | 0.63 | 0.08 | 1.74 | 0.89 | 1.79 |
| ISDGE 1- AMEI/AME (%) | 4.30 | 1.02 | 1.93 | 9.43 | 6.41 | 5.63 | 7.32 | 4.61 | 7.31 |
| ISDGE 2- AMEI/AME (%) | 2.98 | 0.22 | 0.72 | 9.54 | 5.14 | 4.46 | 5.98 | 3.55 | 5.98 |
| CV (%) | | | | | | | | | |
| AME | 6.45 | 6.18 | 4.80 | 6.08 | 7.54 | 8.75 | 3.84 | 4.85 | 6.80 |
| SDGE | 0.47 | 1.01 | 0.77 | 0.77 | 0.69 | 1.14 | 0.53 | 0.73 | 0.55 |
| SDGE1 | 0.44 | 0.95 | 0.73 | 0.73 | 0.65 | 1.08 | 0.50 | 0.69 | 0.52 |
| SDGE2 | 0.45 | 0.95 | 0.72 | 0.72 | 0.66 | 1.09 | 0.51 | 0.70 | 0.53 |

Figure 7:
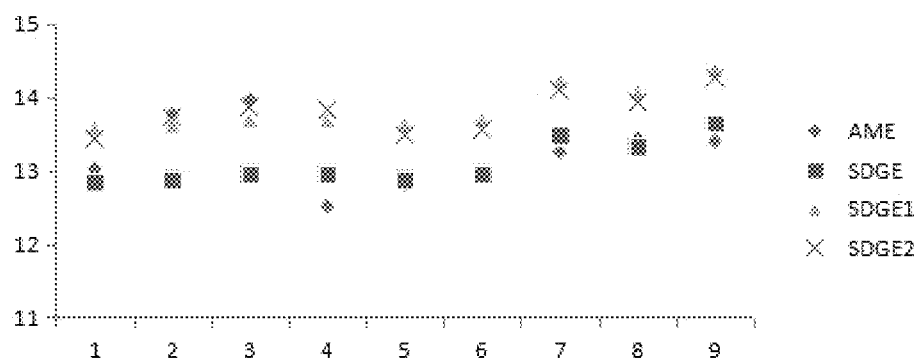
FIG. 7 shows the comparison of measured values of AME, the TME, SDGE, SDGE 1 and SDGE 2 for 9 complete formula feed.

As shown in Table 25, the range of difference between SDGE and AME is −1.01-0.23 MJ/kg, and the relative deviation is 0.08-7.23%. The relative deviation is 1.02-9.43%. The range of difference between SDGE 2 and AME is −0.10-1.32 MJ/kg, and the relative deviation is 0.22-9.54. In all 9 complete diets, there is overlap between AME and SDGE, SDGE 1 and SDGE 2 (FIG. 7). The coefficient of variation of AME is in the range of 3.84-8.75% and the coefficient of variation of SDGE is 0.47-1.14%, indicating that the measuring accuracy for the energy value of simulative digestion gross energy technique is higher than that of the emptying forced feeding technique.

In this example, in the determination of the metabolizable energy of the compound feed by the emptying forced feeding technique, the coefficient of variation does not show an advantage over the coefficient of variation of the feed ingredients in Example 3. This may be related to the wider range of food intake of the goose. Geese can tolerate coarse diets and be mainly raised in a free-range breeding mode before the formation of intensive farming. So far, there are still a large number of free-range farmers who directly feed rice instead of complete diet. The analysis of the coefficient of variation shows that the simulative digestion gross energy technique is better than the biological method in term of either the coefficient of variation for the single feed ingredient in Example 3 or the coefficient of variation for the compound feed in this example. The coefficients of variation for dry matter digestibility, utility rate of apparent energy, and value of simulative digestion gross energy are all less than 3.0%, which is consistent with the acceptable range of coefficient of variation (0.5-3%) of simulative digestion gross energy technique for duck.

Described above are merely preferred embodiments of the present disclosure, it should be noted by those skilled in the art that, several improvements and modifications can be made without departing from the principle of the present disclosure, and these improvements and modifications also should be regarded as the protection scope of the present application and fall into the scope of the present application.

What is claimed is:

1. A method for rapidly estimating metabolizable energy of a goose diet, comprising the following steps:

(1) measuring and calculating, for the diet, a value of simulative digestion gross energy (SDGE) at one or more values of crude fiber wherein measuring and calculating the value of simulative digestion gross energy comprises simulated digestion in a gastric phase and simulated digestion in an intestinal phase, comprising the following steps:

preparing a simulated gastric fluid, a simulated gastric phase buffer, a simulated intestinal fluid, and a simulated intestinal phase buffer;

digesting the diet in the simulated gastric phase buffer containing the simulated gastric fluid and in simulated intestinal phase buffer containing the simulated intestinal fluid in sequence in a monogastric animal simulative digestion device;

collecting and weighing a residue after digestion, and calculating the value of simulative digestion gross energy is according to the following formula D:

$$SDGE = \frac{\text{gross energy of diet} - \text{gross energy of residue}}{\text{mass of diet}}$$

wherein the SDGE is expressed in MJ/kg
wherein during the digestion:
a digestive enzyme in the simulated gastric fluid is pepsin, and the concentration of the pepsin 1475 U/ml;
a digestive enzyme in the simulated intestinal fluid is selected from trypsin, chymotrypsin, and amylase;
a digestion temperature both in a gastric phase and in an intestinal phase is in a range of 40.5-41.5° C.; and a digestion time in the gastric phase is 4-5 hours, and a digestion time in the intestinal phase is in a range of 12-16 hours; and (2) calculating a rectified value of simulative digestion gross energy of the crude fiber in the diet by putting a crude fiber level in the diet to be measured into formula E for rectifying the value of simulative digestion gross energy; wherein formula E comprises:

Rectified value of simulative digestion of gross energy=−0.020*$CF^2$0.333*CF−0.476+SDGE wherein CF represents value of crude fiber level, the unit of the rectified value of simulative digestion gross energy is MJ/kg, and SDGE represents the value of simulative digestion gross energy; and wherein the rectified value of simulative digestion gross energy mapped to the metabolizable energy of the goose diet and the rectified value of simulative digestion gross energy used as a value proximate to the metabolizable energy of the goose diet.

2. The method according to claim 1, wherein:
the rectified value of simulative digestion gross energy is the sum of the value of simulative digestion gross energy obtained by a curve model for rectifying the simulative digestion gross energy and a value of simulative digestion gross energy of the crude fiber in the diet; and
the curve model for the rectified value of simulative digestion gross energy is a quadratic curve regression equation of the crude fiber in cecum against apparent metabolizable energy constructed with the crude fiber being as an independent variable;
wherein the quadratic curve regression equation is expressed by formula C:
wherein formula C comprises:

$$AMEI-AMEC=-0.020*CF^2+0.333*CF-0.476$$

wherein AMEI represents the apparent metabolizable energy in intact geese, AMEC represents the apparent metabolizable energy in cecectomized geese, and CF represents the crude fiber level value.

3. The method according to claim 2, wherein a mass of the crude fiber accounts for 4-11% of a total mass of the diet, and gross energy in the diet containing the crude fiber is 18-22 MJ/kg.

4. The method according to claim 3, wherein the goose is a type of medium-sized goose.

5. The method according to claim 3, wherein an ingredient of the crude fiber is at least one selected from corn, wheat, rice, wheat bran and rice husk.

6. The method according to claim 1, wherein:
when in simulated digestion in the gastric phase, a flow rate of gastric phase buffer solution is 120 ml/min, and a gastric phase buffer solution contains 2.17 g of sodium chloride and 1.57 g of potassium chloride in every 2000 ml of the gastric phase buffer solution, and the gastric phase buffer solution has a pH value of 2.0 at a temperature of 40.5-41.5° C.; and
when in simulated digestion in the intestinal phase, a flow rate of the intestinal phase buffer solution is 120 ml/min, and an intestinal phase buffer solution contains 2.79 g of sodium chloride, 5.33 g of potassium chloride, 41.688 g of anhydrous sodium dihydrogen phosphate, 7.47 g of anhydrous disodium hydrogen phosphate and 1.6 million units of penicillin in every 2000 ml of intestinal phase buffer solution, and the intestinal phase buffer solution has a pH value of 6.38 at a temperature of 40.5° C.-41.5° C.

7. The method according to claim 6, wherein the goose is a type of medium-sized goose.

8. The method according to claim 6, wherein an ingredient of the crude fiber is at least one selected from corn, wheat, rice, wheat bran and rice husk.

9. The method according to claim 1, wherein:
the measuring and calculating comprises a correlation analysis between the value of simulative digestion gross energy and a value of apparent metabolizable energy measured, wherein, in the correlation analysis, an emptying forced feeding technique is performed to obtain a correlation between the value of the apparent metabolizable energy and the value of simulative digestion gross energy, and the measuring accuracy of goose simulative digestion gross energy technique is higher than that of the emptying forced feeding technique, and the value of simulative digestion gross energy is used to construct a calculation formula for the rectified value of simulative digestion gross energy;
wherein the apparent metabolizable energy is calculated according to the following formula A;
wherein formula A comprises:

$$\text{apparent metabolizable energy} = \frac{\text{gross energy of diet} - \text{fecal energy}}{\text{mass of diet}}$$

wherein the emptying forced feeding technique includes a pre-feeding the goose for a period of three days, fasting for 24 hours before the forced feeding, and free drinking during the entire experiment feeding 60 g of air-dried test diet accurately, collecting fecal samples within 48 hours, and collecting endogenous feces on the 11th day after the end of the experiment by starving the goose.

10. The method according to claim 9, wherein the goose is a type of medium-sized goose.

11. The method according to claim 9, wherein an ingredient of the crude fiber is at least one selected from corn, wheat, rice, wheat bran and rice husk.

12. The method according to claim 1, wherein the goose is a type of medium-sized goose.

13. The method according to claim 1, wherein an ingredient of the crude fiber is at least one selected from corn, wheat, rice, wheat bran and rice husk.

14. The method according to claim 1, wherein the goose is a type of medium-sized goose.

15. The method according to claim 1 wherein the goose is a type of medium-sized goose.

16. The method according to claim 1 wherein an ingredient of the crude fiber is at least one selected from corn, wheat, rice, wheat bran and rice husk.

* * * * *